US011523629B2

(12) United States Patent
Ito et al.

(10) Patent No.: US 11,523,629 B2
(45) Date of Patent: Dec. 13, 2022

(54) EMULSION COMPOSITION

(71) Applicant: SAN-EI GEN F.F.I., INC., Toyonaka (JP)

(72) Inventors: Takaaki Ito, Toyonaka (JP); Shota Suzuki, Toyonaka (JP)

(73) Assignee: SAN-EI GEN F.F.I., INC., Toyonaka (JP)

( * ) Notice: Subject to any disclaimer, the term of this patent is extended or adjusted under 35 U.S.C. 154(b) by 0 days.

(21) Appl. No.: 17/050,344

(22) PCT Filed: Apr. 23, 2019

(86) PCT No.: PCT/JP2019/017139
§ 371 (c)(1),
(2) Date: Oct. 23, 2020

(87) PCT Pub. No.: WO2019/208539
PCT Pub. Date: Oct. 31, 2019

(65) Prior Publication Data
US 2021/0235736 A1 Aug. 5, 2021

(30) Foreign Application Priority Data
Apr. 23, 2018 (JP) .............................. JP2018-082402

(51) Int. Cl.
*A23L 29/10* (2016.01)
*A23L 5/44* (2016.01)
(Continued)

(52) U.S. Cl.
CPC .............. *A23L 29/10* (2016.08); *A23C 9/152* (2013.01); *A23D 7/0053* (2013.01); *A23D 7/01* (2013.01);
(Continued)

(58) Field of Classification Search
CPC . A23L 29/10; A23L 5/44; A23L 33/10; A23L 29/219; A23L 29/25; A23L 2/52; A23C 9/152; A23D 7/0053; A23D 7/01
(Continued)

(56) References Cited

U.S. PATENT DOCUMENTS

2007/0286930 A1 12/2007 Ogawa
2011/0081330 A1* 4/2011 Hitzfeld ................. A23L 29/35
424/94.1

(Continued)

FOREIGN PATENT DOCUMENTS

CA      3038782 A1 *   4/2018   ............... A61K 8/06
CN      102056497 B     3/2016
(Continued)

OTHER PUBLICATIONS

International Preliminary Report on Patentability dated Oct. 27, 2020 in International Application No. PCT/JP2019/017139.
(Continued)

*Primary Examiner* — Brent T O'Hern
(74) *Attorney, Agent, or Firm* — Knobbe, Martens, Olson & Bear LLP

(57) ABSTRACT

An emulsion composition includes water, an oily component, gum ghatti and a modified starch. The content of the gum ghatti is 32% by mass or less and the content of the modified starch is 500 parts by mass or less relative to 100 parts by mass of the gum ghatti. The emulsion composition has excellent emulsion stability.

2 Claims, 3 Drawing Sheets

(51) Int. Cl.
    *A23L 33/10*     (2016.01)
    *A23L 29/219*     (2016.01)
    *A23L 29/25*     (2016.01)
    *A23C 9/152*     (2006.01)
    *A23D 7/005*     (2006.01)
    *A23D 7/01*     (2006.01)
    *A23L 2/52*     (2006.01)

(52) U.S. Cl.
    CPC .................. *A23L 2/52* (2013.01); *A23L 5/44* (2016.08); *A23L 29/219* (2016.08); *A23L 29/25* (2016.08); *A23L 33/10* (2016.08)

(58) Field of Classification Search
    USPC ........................................................ 426/602
    See application file for complete search history.

(56) References Cited

U.S. PATENT DOCUMENTS

| | | |
|---|---|---|
| 2012/0149782 A1 | 6/2012 | Hitzfeld |
| 2017/0042808 A1 | 2/2017 | Hirai |
| 2019/0389980 A1 | 12/2019 | Miuchi |

FOREIGN PATENT DOCUMENTS

| | | |
|---|---|---|
| EP | 3 437 488 A1 | 6/2019 |
| JP | H07-101882 A | 4/1995 |
| JP | 2008-013751 A | 1/2008 |
| JP | 2011-521658 A | 7/2011 |
| JP | 2018-052823 A | 4/2018 |
| WO | WO 2009/147158 A2 | 12/2009 |
| WO | WO 2016/031954 A1 | 3/2016 |
| WO | WO 2017/170528 A1 | 10/2017 |
| WO | WO 2018/062554 A1 | 4/2018 |

OTHER PUBLICATIONS

International Search Report, dated Jul. 16, 2019, in International Application No. PCT/JP2019/017139.
Ido et al., Emulsification Properties of GATIFOLIA (Gum Ghatti) Used for Emulsions in Food Products, Food and Food Ingredients Journal of Japan, vol. 213, No. 4, pp. 365-371, 2008.
Extended European Search Report dated Feb. 17, 2021 in European Application No. 19792961.5.
Office Action dated Jun. 23, 2022 in Indonesian Application No. P00202007990.
Office Action dated Oct. 21, 2022 in Taiwanese Patent Application No. 108114140.

* cited by examiner

EMULSION COMPOSITION

PRIORITY AND CROSS REFERENCE TO RELATED APPLICATIONS

This application is the U.S. National Stage Application under 35 U.S.C. § 371 of International Application No. PCT/JP2019/017139, filed Apr. 23, 2019, designating the U.S. and published as WO 2019/208539 A1 on Oct. 31, 2019, which claims the benefit of Japanese Patent Application No. JP 2018-082402, filed Apr. 23, 2018. Any and all applications for which a foreign or a domestic priority is claimed is/are identified in the Application Data Sheet filed herewith and is/are hereby incorporated by reference in their entirety under 37 C.F.R. § 1.57.

TECHNICAL FIELD

The present invention relates to an emulsion composition.

BACKGROUND ART

Heretofore, in order to disperse or dissolve an oily component, e.g., an oil-soluble colorant, an oil-soluble fragrance and an oil-soluble physiologically active substance, in a water-based medium, an emulsion composition in which the oily component is homogenized has been used.

For example, Patent Document 1 proposes an emulsion composition which contains a carotenoid as an oil-soluble colorant and further contains a water-soluble emulsifying agent, tocopherol and lecithin. Patent Document 2 proposes a composition containing gum ghatti, a carotenoid and an oil.

PRIOR ART DOCUMENT

Patent Documents

Patent Document 1: JP-A-2008-13751
Patent Document 2: JP-A-2011-521658

SUMMARY

The present invention addresses the problem of providing an emulsion composition having excellent emulsion stability.

The present inventors have made extensive and intensive studies on emulsion compositions using gum ghatti. As a result, it is found that an emulsion composition prepared using gum ghatti that is a polysaccharide tends to have larger emulsion particle diameters compared with an emulsion composition prepared using a synthetic emulsifying agent such as a sucrose ester of a fatty acid, a polyglycerol ester of a fatty acid and a sorbitan ester of a fatty acid, and that this tendency becomes more significant with the increase in the content of the oily component. When the emulsion particle diameters in an emulsion composition are large, in order to make it possible to use the emulsion composition in a beverage for example, it is needed to make a kind of effort such that the specific gravity of the beverage is matched to that of the oily phase using a specific gravity modifier in the oily phase. The present inventors have made further extensive and intensive studies. As a result, it is found that, when a specified amount of a modified starch is used together with gum ghatti, even if the content of an oily component is large, it is possible to provide an emulsion composition having very small emulsion particle diameters and a narrow particle size distribution and also having excellent emulsion stability. The present invention has been accomplished on the basis of these findings.

The present invention includes the following aspects.

Item 1.
An emulsion composition comprising water, an oily component, gum ghatti and a modified starch,
wherein
the content of the gum ghatti is 32% by mass or less, and
the content of the modified starch is 500 parts by mass or less relative to 100 parts by mass of the gum ghatti.

Item 2.
The emulsion composition according to item 1, wherein the gum ghatti is low-molecular-weight gum ghatti.

Item 3.
The emulsion composition according to item 1 or 2, wherein the low-molecular-weight gum ghatti has a weight average molecular weight of $0.020 \times 10^6$ to $1.10 \times 10^6$.

Item 4.
The emulsion composition according to any one of items 1 to 3, wherein the content of the modified starch relative to 100 parts by mass of the oily component is 0.01 to 35 parts by mass.

Item 5.
The emulsion composition according to any one of items 1 to 4, wherein the oily component comprises one or more component selected from the group consisting of an oil-soluble colorant, an oil-soluble fragrance, an oil-soluble physiologically active substance and an oil-based solvent.

Item 6.
The emulsion composition according to any one of items 1 to 5, wherein the oily component comprises a carotenoid colorant.

Item 7.
The emulsion composition according to any one of items 1 to 6, wherein the oily component comprises an oil-soluble fragrance.

Item 8.
The emulsion composition according to any one of items 1 to 7, wherein the emulsion composition has a liquid, powdery, granular or tablet-like form.

Item 9.
A method for producing an emulsion composition, comprising steps of:
preparing a mixed solution comprising water, an oily component, gum ghatti and a modified starch, wherein the content of the gum ghatti is 32% by mass or less and the content of the modified starch is 500 parts by mass or less relative to 100 parts by mass of the gum ghatti in the mixed solution; and
homogenizing the mixed solution.

Item 10.
A method for producing a powdery, granular or tablet-like composition, comprising a step of powderizing an emulsion composition as recited in item 9.

Item 11.
The method according to item 9 or 10, wherein an organic solvent is not used.

Item 12.
A method for producing a composition selected from the group consisting of a food or beverage, a cosmetic product, a drug, a quasi-drug, a sanitary household product and a feed, comprising a step of dissolving or dispersing an emulsion composition as recited in any one of items 1 to 8 or a powdery, granular or tablet-like composition as recited in item 10 in a water-based solvent.

Item 13.

A food or beverage, a cosmetic product, a drug, a quasi-drug, a sanitary household product or a feed, which comprises an emulsion composition as recited in any one of items 1 to 8 or a powdery, granular or tablet-like composition as recited in item 10.

According to the present invention, it becomes possible to provide an emulsion composition having very small emulsion particle diameters and a narrow particle size distribution and also having excellent emulsion stability even when the content of an oily component is large, by using a specified amount of a modified starch in combination with gum ghatti.

MODE FOR CARRYING OUT THE INVENTION

Figure 1:
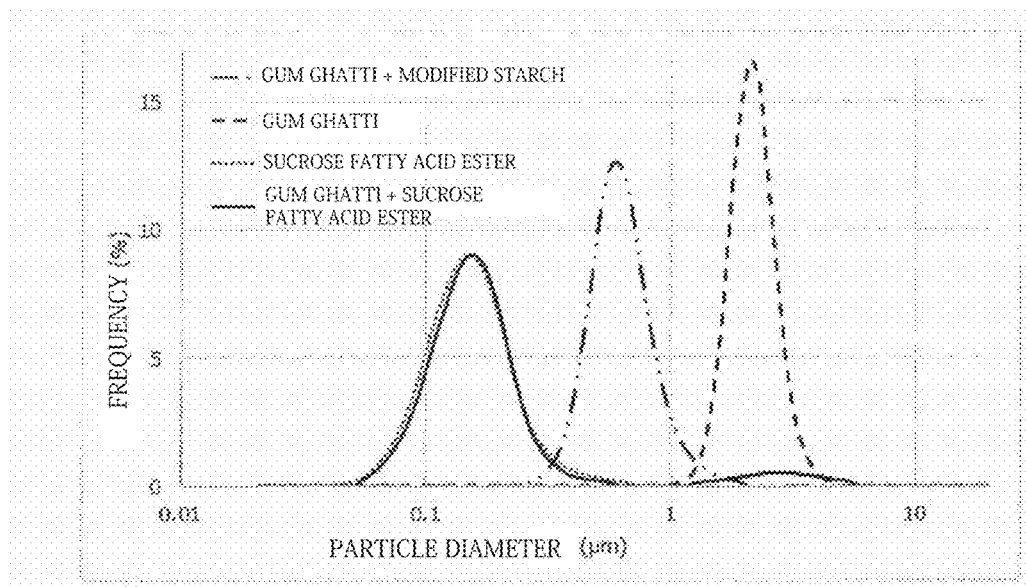
FIG. 1 illustrates graphs showing the particle size distributions of emulsion particles in emulsion compositions in Experiment Example 3.

The present invention relates to an emulsion composition. Hereinbelow, the embodiment of the present invention will be described in detail.

The term "comprises (comprising)" as used herein is intended to include both of the wording "substantially consisting of" and the wording "consisting of".

1. Emulsion Composition

The emulsion composition of the present invention can be preferably an oil-in-water-type emulsion composition.

More specifically, the emulsion composition of the present invention can preferably contain: an aqueous phase that is a continuous phase containing water as a medium; and an oily phase that is in the form of particles each containing an oil-soluble material and/or an oil-based solvent (wherein the particles are also referred to "oil-containing particles" in the description).

Water

Examples of water to be used in the present invention include pure water, ion-exchange water and tap water.

The content of water can be, but not limited to, for example, 5% by mass or more, preferably 10% by mass or more, more preferably 15% by mass or more, still more preferably 20% by mass or more, particularly preferably 25% by mass or more, relative to the whole amount of the composition. The content of water can be, but not limited to, for example, 60% by mass or less, preferably 55% by mass or less, more preferably 50% by mass or less, still more preferably 45% by mass or less, particularly preferably 35% by mass or less, relative to the whole amount of the composition. The content of water can be, but not limited to, for example, 5 to 60% by mass, 5 to 55% by mass, 5 to 50% by mass, 5 to 45% by mass, 5 to 40% by mass, 10 to 60% by mass, 10 to 55% by mass, 10 to 50% by mass, 10 to 45% by mass, or 10 to 40% by mass, relative to the whole amount of the composition.

Oily Component

The oily component (i.e., a component constituting the oily phase) to be used in the present invention comprises at least one component selected from the group consisting of an oil-soluble material (including a fat-soluble material) and an oil-based solvent. The term "oily" as used herein can refer to a property that the solubility in one or both of n-hexane and ethyl acetate at 20° C. is 10 g/L or more (preferably 50 g/L).

Oil-Soluble Material

Examples of the oil-soluble material to be used in the present invention include an oil-soluble colorant, an oil-soluble fragrance and an oil-soluble physiologically active substance.

Oil-Soluble Colorant

The oil-soluble colorant (including a fat-soluble colorant) to be used in the present invention is not limited, as long as the oil-soluble colorant is an oil-soluble or fat-soluble substance containing a coloring component.

The oil-soluble colorant to be used in the present invention is preferably an edible colorant that can be added to foods and beverages or a colorant that is applicable to human bodies in the form of a cosmetic product containing the colorant.

The oil-soluble colorant is not limited, as long as the effect of the present invention can be exerted. An example is a carotenoid colorant. The carotenoid colorant may be a natural colorant containing a carotenoid. Examples of the carotenoid colorant include:

a carotene such as tomato pigment, *dunaliella* carotene, carrot carotene, palm oil carotene, lycopene, phytoene, phytofluene, α-carotene and β-carotene;

a xanthophyll such as paprika pigment, marigold pigment, *Haematococcus algae* pigment, capsanthin, capsorubin, lutein, zeaxanthin, astaxanthin, canthaxanthin, β-cryptoxanthin, violaxanthin, actinioerythritol, cucurbitaxanthin A, cryptocapsin, fucoxanthin, shrimp pigment, krill pigment and crayfish pigment;

an apocarotenoid such as annatto extract, bixin, β-8'-apo-carotenal (apocarotenal), β-12'-apo-carotenal and derivatives thereof (e.g., an ester with a lower or higher alcohol), crocetin and mycorradicin; and turmeric oleoresin, crucumin, and chlorophyll. These oil-soluble colorants may be used singly, or any two or more of them may be used in combination.

Oil-Soluble Fragrance

The oil-soluble fragrance (including a fat-soluble fragrance) to be used in the present invention is not limited, as long as the oil-soluble fragrance is an oil-soluble or fat-soluble substance containing a fragrance ingredient.

The oil-soluble fragrance to be used in the present invention is preferably an edible fragrance that can be added to foods and beverages or a fragrance that is applicable to human bodies in the form of a cosmetic containing the fragrance.

Examples of the fragrance include:

an extract produced from an animal- or plant-derived natural raw material by extraction with a non-volatile solvent, extraction with a volatile solvent, supercritical extraction or a combination of them;

a natural fragrance such as an essential oil produced by hydrostillation, a squeeze method or the like, and a recovered fragrance;

a synthetic fragrance which is a fragrance synthesized by a chemical technique; and a fragrance base prepared by adding and/or dissolving any one of these fragrances in an oil or fat and/or a solvent.

Examples of the form of the natural fragrance include:

an extract such as an absolute, an essence, and an oleoresin;

a squeezed liquid obtained by cold pressing or the like; and an extract with an alcohol or an extract with a mixed solution of water and an alcohol (i.e., a so-called "tincture").

Specific examples of these fragrances include:

a citrus fruit essential oil such as orange oil, lemon oil, grapefruit oil, lime oil and mandarin oil;

a flower essential oil (or absolute) such as lavender oil;

an essential oil such as peppermint oil, spearmint oil and cinnamon oil;

an essential oil (or oleoresin) of a spice such as allspice, anise seed, basil, laurel, cardamom, celery, clove, garlic, ginger, mustard, onion, paprika, parsley and black pepper;

a synthetic fragrance such as limonene, linalool, geraniol, menthol, eugenol and vanillin;

an extracted oil derived from beans such as coffee, cacao, vanilla and roasted peanut;

an essential derived from tea such as black tea, green tea and oolong tea; and a synthetic fragrance compound.

These fragrances may be used singly. In general, a combination of any two or more of them is used as a mixed fragrance.

The term "fragrance" as used is defined as a concept including a fragrance (or flavor) composed of a single compound as well as a mixed fragrance (or flavor).

Oil-Soluble Physiologically Active Substance

The oil-soluble physiologically active substance (including a fat-soluble physiologically active substance) to be used in the present invention is not limited, as long as the oil-soluble physiologically active substance is an oil-soluble or fat-soluble substance that is useful for a living body.

The oil-soluble physiologically active substance to be used in the present invention is preferably an edible substance that can be added to a food or beverage, or a substance that is applicable to human bodies in the form of a cosmetic product containing the substance.

Examples of the oil-soluble physiologically active substance include:

an oil-soluble drug;

a fat-soluble vitamin such as liver oil, vitamin A (e.g., retinol), vitamin A oil, vitamin D (e.g., ergocalciferol, cholecalciferol), vitamin $B_2$ tetrabutyrate, an ascorbic acid fatty acid ester, vitamin E (e.g., tocopherol, tocotrienol, tocopheryl acetate), and vitamin K (e.g., phylloquinone, menaquinone);

a plant-derived essential oil such as limonene, linalool, nerol, citronellol, geraniol, citral, l-menthol, eugenol, cinnamic aldehyde, anethole, *perilla* aldehyde, vanillin and γ-undecalactone;

resveratrol, oil-soluble polyphenol, glycosylceramide, sesamin, phosphatidylserine, coenzyme Q10, ubiquinol and α-lipoic acid a Ω-3-type fatty acid such as α-linolenic acid, eicosapentaenoic acid and docosahexaenoic acid;

an Ω-6-type fatty acid such as linoleic acid and γ-linolenic acid; and a functional material such as a plant sterol.

Among these substances, preferred examples include: a fat-soluble vitamin, coenzyme Q10 and lipoic acid; and an Ω-3-type fatty acid such as α-linolenic acid, eicosapentaenoic acid and docosahexaenoic acid.

These oil-soluble physiologically active substances may be used singly, or any two or more of them may be used in combination.

Oil-Based Solvent

The oil-based solvent to be used in the present invention is preferably a solvent that can be used as a solvent for the oil-soluble material, specifically a solvent that is compatible with the oil-soluble material.

The oil-based solvent to be used in the present invention is preferably an edible substance that can be added to foods and beverages, or a substance that is applicable to human bodies in the form of a cosmetic product containing the substance.

Examples of the oil-based solvent to be used in the present invention include:

a plant-derived oil or fat such as rapeseed oil, corn oil, palm oil, soybean oil, olive oil, jojoba oil, coconut oil, elemi resin and mastic resin;

an animal-derived oil or fat such as beef tallow and pork fat; and sucrose acetate isobutyrate ester (SAIB), rosin, dammar resin, ester gum, a glycerin fatty acid ester and triglyceride.

These solvents may be used singly, or any two or more of them may be used in combination.

Specific examples of the oil-based solvent preferably include a plant-derived oil or fat, sucrose acetate isobutyrate ester (SAIB), a glycerin fatty acid ester and triglyceride, more preferably a plant-derived oil or fat, a glycerin fatty acid ester and triglyceride (still more preferably a medium-chain fatty acid triglyceride (MCT)).

The content of the oily component in the emulsion composition of the present invention is, but not particularly limited to, preferably 0.3 to 60% by mass, more preferably 0.5 to 55% by mass, still more preferably 0.5 to 50% by mass, furthermore preferably 0.8 to 47% by mass, particularly preferably 1 to 40% by mass, relative to the whole amount of the composition.

In general, the emulsion stability of an emulsion composition tends to be deteriorated with the increase in the content of an oily component. According to the present invention, however, an emulsion composition having excellent emulsion stability can be provided even when the content of the oily component is, for example, 5% by mass or more, 6% by mass or more, 7% by mass or more, 8% by mass or more, 9% by mass or more, 10% by mass or more, 11% by mass or more, 12% by mass or more, 13% by mass or more, 14% by mass or more, 15% by mass or more, 16% by mass or more, 17% by mass or more, 18% by mass or more, 19% by mass or more, 20% by mass or more, 21% by mass or more, 22% by mass or more, 23% by mass or more, 24% by mass or more, or 25% by mass or more, relative to the whole amount of the composition.

Gum Ghatti

Gum ghatti is a polysaccharide derived from a sap (secretory fluid) of *Anogeissus latifolia*, and is known as a thickening stabilizer (a food additive). The gum ghatti to be used in the present invention is commercially available, and an example thereof is "gum ghatti RD" manufactured by San-Ei Gen F.F.I., Inc.

The gum ghatti may be, but not limited to, gum ghatti of which the molecular weight is reduced (i.e., low-molecular-weight gum ghatti). The weight average molecular weight of low-molecular-weight gum ghatti can be, but not limited to, for example, $0.020 \times 10^6$ to $1.10 \times 10^6$, preferably $0.020 \times 10^6$ to $0.90 \times 10^6$, more preferably $0.020 \times 10^6$ to $0.60 \times 10^6$, still more preferably $0.025 \times 10^6$ to $0.50 \times 10^6$, furthermore preferably $0.030 \times 10^6$ to $0.40 \times 10^6$, particularly preferably $0.030 \times 10^6$ to $0.35 \times 10^6$, more particularly preferably $0.040 \times 10^6$ to $0.35 \times 10^6$.

The molecular weight and the distribution thereof of gum ghatti can be measured by the following method.

[Method for Measuring Molecular Weight and Molecular Weight Distribution]

The molecular weight and the molecular weight distribution are measured by GPC analysis under the following conditions.

Detector: RI
Mobile phase: 100 mM $K_2SO_4$
Flow rate: 1.0 ml/min
Temperature: 40° C.
Column: TSKgel GMPWXL 30 cm (Guard PWXL)
Injection: 100 μl
Pullulan standard: Shodex STANDARD P-82

Method for Producing Low-Molecular-Weight Gum Ghatti

The low-molecular-weight gum ghatti to be used in the present invention can be produced by, for example, the below-mentioned production method or a method analogous thereto. The method for producing low-molecular-weight gum ghatti to be used in the present invention includes a step of subjecting gum ghatti that is a raw material to a molecular weight reduction treatment. As the gum ghatti that is a raw material, commercially available gum ghatti can be used.

The weight average molecular weight of gum ghatti that has been distributed in the market is generally $1.1 \times 10^6$ to $2 \times 10^6$. The gum ghatti to be used as a raw material is not particularly limited, as long as gum ghatti having a desired molecular weight can be produced. The gum ghatti may originally contain low-molecular-weight gum ghatti as a portion thereof.

The method for the molecular weight reduction treatment in the production method is not particularly limited. One preferred example of the method includes a molecular weight reduction treatment in the presence of water, such as at least one treatment method selected from the group consisting of a thermal decomposition treatment, an acid decomposition treatment and an enzymatic decomposition treatment.

In the thermal decomposition treatment, the conditions under which gum ghatti having a desired weight average molecular weight can be produced can be selected and performed appropriately on the basis of the common technical knowledge.

In general, gum ghatti having a smaller weight average molecular weight can be produced at a higher treatment temperature.

Concretely, the treatment temperature for the thermal decomposition treatment may be, for example, 60 to 200° C., preferably 80 to 200° C.

In general, gum ghatti having a smaller weight average molecular weight can be produced with a longer treatment time.

Concretely, the treatment time for the thermal decomposition treatment may be, for example, 30 seconds to 8 hours. The time can be selected appropriately depending on the treatment temperature for the thermal decomposition treatment. For example, a shorter treatment time can be selected when the treatment temperature is higher.

The thermal decomposition treatment can be carried out satisfactorily under the pH condition of, for example, 5 or lower.

Examples of the acid to be used in the acid decomposition treatment include citric acid (including anhydrous citric acid), phosphoric acid, phytic acid, malic acid, tartaric acid, hydrochloric acid, acetic acid, lactic acid and ascorbic acid.

These acids may be used singly, or two or more of them may be used in combination.

In general, gum ghatti having a smaller weight average molecular weight can be produced at a higher treatment temperature.

The treatment temperature for the acid decomposition treatment may be, for example, 60 to 200° C.

In general, gum ghatti having a smaller weight average molecular weight can be produced with a longer treatment time.

The treatment time for the acid decomposition treatment may be, for example, 30 seconds to 8 hours.

The acid decomposition treatment can be carried out satisfactorily under the pH condition of, for example, 4 or lower.

Examples of the enzyme to be used in the enzymatic decomposition treatment include; cellulase; mannanase; pectinase; sucrase; hemicellulase; Cellulosin AC40, Cellulosin HC100, Cellulosin TP25 and Cellulosin GM5 (manufactured by HBI Enzymes Inc.); Sumizyme PX and Sumizyme AG2-L (manufactured by Shinnihon Chemicals Corporation); Macerozyme A (manufactured by Yakult Pharmaceutical Industry Co., Ltd.); and Macerating Enzyme Y (manufactured by Yakult Pharmaceutical Industry Co., Ltd.).

These enzymes may be used singly, or two or more of them may be used in combination.

The conditions (e.g., temperature, time, pH, additives) for the enzymatic treatment may be selected appropriately depending on the types of the enzyme to be used.

From the viewpoint of exerting the effect of the present invention significantly, the content of gum ghatti in the emulsion composition of the present invention is 32% by mass or less, preferably 30% by mass or less, more preferably 20% by mass or less, still more preferably 15% by mass or less, particularly preferably 10% by mass or less, most preferably 8% by mass or less, relative to the whole amount of the composition. The content of gum ghatti in the emulsion composition can be 0.5% by mass or more, preferably 1% by mass or more, more preferably 3% by mass or more, still more preferably 4% by mass, furthermore preferably 5% by mass or more, particularly preferably 6% by mass or more, relative to the whole amount of the composition. Examples of the content of gum ghatti in the emulsion composition include 0.5 to 32% by mass, 0.5 to 30% by mass, 0.5 to 20% by mass, 0.5 to 15% by mass, 0.5 to 10% by mass, 0.5 to 8% by mass, 1 to 32% by mass, 1 to 30% by mass, 1 to 20% by mass, 1 to 15% by mass, 1 to 10% by mass, 1 to 8% by mass, 3 to 32% by mass, 3 to 30% by mass, 3 to 20% by mass, 3 to 15% by mass, 3 to 10% by mass, 3 to 8% by mass, 4 to 32% by mass, 4 to 30% by mass, 4 to 20% by mass, 4 to 15% by mass, 4 to 10% by mass, 4 to 8% by mass, 5 to 32% by mass, 5 to 30% by mass, 5 to 20% by mass, 5 to 15% by mass, 5 to 10% by mass, 5 to 8% by mass, 6 to 32% by mass, 6 to 30% by mass, 6 to 20% by mass, 6 to 15% by mass, 6 to 10% by mass and 6 to 8% by mass, all relative to the whole amount of the composition.

In the case where the content of the oily component in the emulsion composition is 5% by mass or more, the content of gum ghatti relative to 100 parts by mass of the oily component is preferably 4 to 100 parts by mass, more preferably 5 to 80 parts by mass, still more preferably 8 to 70 parts by mass, furthermore preferably 10 to 50 parts by mass.

Modified Starch

The modified starch to be used in the present invention is a starch produced by subjecting a raw material starch, i.e., a starch derived from corn, potato, sweet potato, wheat, non-glutinous rice, glutinous rice, tapioca, sago or the like, to a chemical treatment which is roughly classified into a decomposition-type treatment and an addition-type treatment, a physical processing treatment such as a wet-heat treatment, or the like.

These starch raw materials may be used singly, or any two or more of them may be used in combination.

The starch raw material is preferably corn or tapioca. As the varieties of corn, dent corn, flint corn, flour corn, sweet corn, popcorn and waxy (glutinous) corn are known.

In the present invention, the starch raw material is not particularly limited, and any variety of corn can be used as the starch raw material. A preferred example of the starch raw material is corn of waxy variety of which starch is glutinous (wherein the corn of this type is simply referred to as "waxy corn" in the description).

Examples of the modified starch to be used in the present invention include acetylated distarch adipate, acetylated oxidized starch, acetylated distarch phosphate, oxidized starch, hydroxypropyl starch, hydroxypropyl distarch phosphate, carboxymethyl starch, starch acetate, starch octenyl succinate, monostarch phosphate, distarch phosphate and phosphated distarch phosphate which can be produced by processing the above-mentioned raw material starch, preferably hydroxypropyl starch, hydroxypropyl distarch phosphate and starch octenyl succinate, more preferably starch octenyl succinate.

These modified starches may be used singly, or any two or more of them may be used in the form of a mixture.

From the viewpoint of exerting the effect of the present invention significantly, the content of the modified starch in the emulsion composition of the present invention is 500 parts by mass or less, preferably 300 parts by mass or less, more preferably 200 parts by mass or less, still more preferably 100 parts by mass or less, furthermore preferably 80 parts by mass or less, particularly preferably 50 parts by mass or less, more particularly preferably 35 parts by mass or less, most preferably 25 parts by mass or less, relative to 100 parts by mass of gum ghatti. The content of the modified starch in the emulsion composition is, for example, 0.01 parts by mass or more, preferably 0.1 parts by mass or more, more preferably 0.5 parts by mass or more, still more preferably 1 part by mass or more, furthermore preferably 3 parts by mass or more, particularly preferably 5 parts by mass or more, more particularly preferably 8 parts by mass or more, most preferably 10 parts by mass or more, relative to 100 parts by mass of gum ghatti. The content of the modified starch in the emulsion composition is, for example, 0.01 to 500 parts by mass, preferably 0.1 to 300 parts by mass, more preferably 0.5 to 200 parts by mass, still more preferably 1 to 100 parts by mass, furthermore preferably 3 to 80 parts by mass, particularly preferably 5 to 50 parts by mass, more particularly preferably 8 to 35 parts by mass, most preferably 10 to 25 parts by mass, relative to 100 parts by mass of gum ghatti.

In the present invention, the content of the modified starch can be adjusted appropriately within the above-mentioned content range, depending on the content of the oily component in the emulsion composition.

The content of the modified starch in the emulsion composition of the present invention is not particularly limited, and is preferably 0.0005 to 7% by mass, more preferably 0.001 to 7% by mass, still more preferably 0.005 to 6% by mass, furthermore preferably 0.01 to 5% by mass, and the content of the modified starch can be adjusted appropriately depending on the content of the oily component in the emulsion composition.

The preferred content of the modified starch relative to 100 parts by mass of the oily component is not particularly limited, and is 0.01 to 35 parts by mass, and the content of the modified starch can be adjusted appropriately depending on the content of the oily component in the emulsion composition. More preferred content of the modified starch relative to 100 parts by mass of the oily component is 0.1 to 30 parts by mass, still more preferably 0.2 to 28 parts by mass, furthermore preferably 0.3 to 25 parts by mass, furthermore preferably 0.3 to 22 parts by mass, furthermore preferably 0.3 to 20 parts by mass.

Emulsion Particle Diameter

The (volume-based) median diameter of emulsion particles in the emulsion composition can be, but is not limited to, 20 μm or less, preferably 15 μm or less, more preferably 10 μm or less, still more preferably 9 μm or less, particularly preferably 8 μm or less. It is preferred that the (volume-based) median diameter is determined in, but not limited to, a pre-emulsified state wherein an aqueous phase comprising water, gum ghatti and the modified starch is mixed with an oily phase comprising the oily component under the conditions of 3000 rpm for 5 minutes, for example.

The lower limit of the (volume-based) median diameter is not particularly limited, and can be adjusted appropriately depending on the types of the desired emulsion composition.

In the present description, the (volume-based) median diameter of the emulsion particles in the emulsion composition can be determined in the following manner. A particle size distribution of a sample is measured using a laser diffraction/scattering particle size distribution measurement device such as Microtrac MT3000EX-II (MicrotracBEL Corporation) to produce a volume-based cumulative particle size distribution curve. In the produced cumulative particle size distribution curve, a volume cumulative particle diameter at a cumulative volume of 50% by volume (D50) in a particle size distribution that is measured in terms of particle diameter as observed from the smaller particle side at 50% cumulation is a median diameter of the emulsion particles in the emulsion composition. The (volume-based) median diameter of the emulsion particles in the emulsion composition is described in detail in the section "EXAMPLES" below.

The emulsion composition of the present invention has excellent emulsion stability. Therefore, the median diameter of the emulsion particles can be further reduced by carrying out a homogenization treatment using a high-pressure homogenizer, a homodisper, a homomixer, a polytron-type stirrer, a colloid mill, a nanomizer or the like. For example, the homogenization treatment using a high-pressure homogenizer can be carried out, but is not limited to, five passes using a homogenizer (15MR-8TA, manufactured by MANTON-GAULIN) at 560 kg/cm$^2$.

In the case where the homogenization treatment is carried out, the (volume-based) median diameter of the emulsion particles in the emulsion composition is, but not limited to, 2 μm or less, preferably 1.8 μm or less, more preferably 1.5 μm or less, still more preferably 1 μm or less, furthermore preferably 0.8 μm or less, particularly preferably 0.6 μm or less, more particularly preferably 0.5 μm or less, still more particularly preferably 0.42 μm or less, most preferably 0.3 μm or less. The emulsion composition of the present invention has excellent long-term storage stability. Therefore, it is preferred, but is not limited, to maintain the above-mentioned (volume-based) median diameter even when the emulsion composition is stored at 60° C. for 7 days.

In the case where the homogenization treatment is carried out, the frequency of the particle diameter of 1.3 μm or more of the emulsion particles in the emulsion composition is, but not limited to, 60% or less, preferably 40% or less, more preferably 15% or less, still more preferably 10% or less, furthermore preferably 8% or less, particularly preferably 5% or less, most preferably 2% or less. The emulsion composition of the present invention has excellent long-term storage stability. Therefore, it is preferred, but is not limited, to maintain the frequency of the particle diameter of 1.3 μm or more of the emulsion particles in the emulsion composition even when the emulsion composition is stored at 60° C. for 7 days.

The emulsion composition of the present invention can have excellent storage stability properties due to the use of gum ghatti and the modified starch in combination. It is preferred, but is not limited to, that the emulsion composition of the present invention does not cause oil/water separation even when the emulsion composition is stored at 60° C. for 7 days.

According to the present invention, it is also possible to prepare an emulsion composition in which the (volume-based) median diameter of emulsion particles is smaller, such as an emulsion composition in which the median diameter is preferably less than 0.3 μm, more preferably 0.25 μm or less, still more preferably 0.2 μm or less.

Heretofore, when an emulsion composition using gum ghatti is dissolved or dispersed in a water-based solvent, cloudiness is often imparted to the emulsion composition. According to one embodiment of the present invention, in contrast, it is possible to provide a clear emulsion composition which can be dissolved or dispersed in a water-based medium in a clear state. Heretofore, in the case where an emulsion composition in which gum ghatti is used but a specific gravity modifier (e.g., SAIB) is not contained in an oily phase is used in a beverage, a phenomenon that emulsion particles float on the upper surface of the beverage is likely to occur. However, by using an emulsion composition having a median diameter of less than 0.3 μm, a stable beverage can be provided without the need to use a specific gravity modifier.

The clear emulsion composition can be prepared by, for example, adjusting the content of the oily component to 10% by mass or less, preferably 5% by mass or less.

Furthermore, according to the present invention, it is also possible to prepare an emulsion composition in which the content of the oily component is more than 10% by mass and the median diameter is less than 0.3 μm. In this case, the lower limit of the median diameter in the emulsion composition may be, but not particularly limited to, for example, 0.05 μm or more.

Polyhydric Alcohol

The emulsion composition of the present invention can preferably contain a polyhydric alcohol. In this case, the storage stability of the emulsion composition can be improved.

Examples of the polyhydric alcohol to be used in the present invention include glycerine, diglycerine, triglycerol, polyglycerol, propylene glycol, dipropylene glycol, 1,3-butylene glycol, ethylene glycol, polyethylene glycol, sorbitol (D-sorbitol), xylitol, maltitol, erythritol, mannitol, xylose, glucose, lactose, mannose, oligotose, fructose-glucose syrup and sucrose.

These polyhydric alcohols may be used singly, or any two or more of them may be used in combination.

In the present invention, the polyhydric alcohol preferably comprises propylene glycol, glycerin or a combination thereof.

The content of the polyhydric alcohol in the emulsion composition of the present invention is not particularly limited, and can be adjusted appropriately depending on the types of the desired emulsion composition. The content of the polyhydric alcohol in the emulsion composition is, for example, 10% by mass or more, preferably 15% by mass or more, more preferably 20% by mass or more, still more preferably 25% by mass or more, relative to the whole amount of the composition. The upper limit of the content of the polyhydric alcohol is not particularly limited and is, for example, 60% by mass or less, preferably 58% by mass or less, more preferably 55% by mass or less, still more preferably 50% by mass or less, relative to the whole amount of the composition. Therefore, the content of the polyhydric alcohol in the emulsion composition is, for example, 10 to 60% by mass, preferably, 15 to 58% by mass, more preferably, 20 to 55% by mass, still more preferably, 25 to 50% by mass, relative to the whole amount of the composition.

When a polyhydric alcohol is added to an emulsion composition, emulsion particles in the emulsion composition may become large. However, according to the present invention, an emulsion composition in which the median diameter of emulsion particles falls within the above-mentioned range can be provided.

pH

The pH value of the emulsion composition of the present invention can be adjusted appropriately depending on the types or contents of the blend components, the types of the intended form of the emulsion composition or the like. The pH value can be, but not limited to, for example, 2 to 8, 2.5 to 7.5, or 3 to 7. In the case where the emulsion composition of the present invention has a liquid form, it is desirable that the pH value falls within the range from 2 to 4, preferably from 2.5 to 3.5. In order to adjust the pH value of the emulsion composition to a value falling within the above-mentioned range, an organic acid and/or an inorganic acid may be used if necessary. The type of the organic acid and/or the inorganic acid is not particularly limited.

Examples of the organic acid and/or the inorganic acid include citric acid, phytic acid, ascorbic acid, phosphoric acid, lactic acid, adipic acid, gluconic acid, succinic acid, acetic acid, tartaric acid, fumaric acid, malic acid and pyrophosphoric acid. These organic acids and/or the inorganic acids may be used singly, or any two or more of them may be used in combination.

In the present invention, the organic acid and/or the inorganic acid preferably are/is one or more acid selected from the group consisting of citric acid, phytic acid, ascorbic acid, phosphoric acid and lactic acid.

The emulsion composition of the present invention may contain a water-soluble vitamin, a thickening stabilizer, an antioxidant agent, a chelating agent, an oxidation inhibitor and the like as other arbitrary components, as long as the effect of the present invention is not inhibited. The emulsion composition of the present invention may contain ethanol to such an extent that the effect of the present invention is not inhibited.

The emulsion composition of the present invention may contain other emulsifying gent in such an extent that the effect of the present invention is not inhibited. One preferred example of the emulsifying agent includes lecithin (including lecithin, enzymatically decomposed lecithin, and enzymatically treated lecithin).

Method for Producing Emulsion Composition

The present invention also relates to a method for producing an emulsion composition as mentioned below.

A method for producing an emulsion composition, comprising steps of:

preparing a mixed solution comprising water, an oily component, gum ghatti and a modified starch, wherein the content of the gum ghatti is 32% by mass or less and the content of the modified starch is 500 parts by mass or less relative to 100 parts by mass of the gum ghatti in the mixed solution; and homogenizing the mixed solution.

In the production method of the present invention, the means, methods and conditions for the step of preparing the mixed solution and for the step of homogenizing are not particularly limited, as long as an emulsion composition comprising water, gum ghatti, a modified starch and an oily component can be prepared. For example, in the case where the emulsion composition can be prepared by a treatment of mixing water, gum ghatti, the modified starch and the oily component with one another, the preparation step and the homogenization treatment step for the mixed solution may be carried out in a single process (the same process).

The homogenization treatment may be one using an emulsifying machine such as a homogenizer (e.g., a high-pressure homogenizer, a homodisper, a homomixer, a polytron-type stirrer, a colloid mill and a nanomizer). The conditions for the homogenization treatment may be selected appropriately depending on the types of the emulsifying machines to be used and the like.

The form of the emulsion composition of the present invention is not particularly limited, may be appropriately prepared into a liquid form, a powdery, a granular or a tablet-like form depending on the types of a product, e.g., a food or beverage, a cosmetic product (including a beauty product), a drug and a quasi-drug, to which the emulsion composition is to be applied. For example, in the emulsion composition of the present invention, the particles in the emulsion composition may be powderized by a powderization means. The powderization means may be carried out in the conventional manner. For example, a means such as spray drying or freeze drying may be employed. In the powderization, a proper carrier or the like may be added. Alternatively, the emulsion composition of the present invention may be in a liquid form prepared by dispersing the above-mentioned powderized product in a water-based solvent again.

From this viewpoint, the present invention also relates to a method for producing a powdery, granular or tablet-like composition, comprising the following embodiment.

A method for producing a powdery, granular or tablet-like composition, comprising steps of:

preparing a mixed solution comprising water, an oily component, gum ghatti and a modified starch, wherein the content of the gum ghatti is 32% by mass or less and the content of the modified starch is 500 parts by mass or less relative to 100 parts by mass of the gum ghatti in the mixed solution;

homogenizing the mixed solution to prepare an emulsion composition; and powderizing the emulsion composition.

The powdery, granular or tablet-like composition thus produced has such advantages that the dispersibility in a water-based medium and the emulsion stability after the dispersion are excellent. The powderization treatment is not particularly limited, and can be carried out in the conventional manner. The powderization treatment includes, for example, a spray drying method or a freeze drying method.

In the case where the composition of the present invention is prepared into the powdery, granular or tablet-like preparation as one embodiment of the present invention, the content of gum ghatti in the composition can be, for example, 1 to 32% by mass, 3 to 32% by mass, 5 to 32% by mass, 7 to 32% by mass, 10 to 32% by mass, 13 to 32% by mass, 15 to 32% by mass, 1 to 30% by mass, 3 to 30% by mass, 5 to 30% by mass, 7 to 30% by mass, 10 to 30% by mass, 13 to 30% by mass, 15 to 30% by mass, 1 to 25% by mass, 3 to 25% by mass, 5 to 25% by mass, 7 to 25% by mass, 10 to 25% by mass, 13 to 25% by mass, 15 to 25% by mass, 1 to 20% by mass, 3 to 20% by mass, 5 to 20% by mass, 7 to 20% by mass, 10 to 20% by mass, 13 to 20% by mass or 15 to 20% by mass, relative to the whole amount of the composition.

In the case where the composition of the present invention is prepared into the powdery, granular or tablet-like preparation as one embodiment of the present invention, the content of the modified starch in the composition can be, for example, 0.01 to 15% by mass, 0.05 to 15% by mass, 0.1 to 15% by mass, 0.5 to 15% by mass, 1 to 15% by mass, 2 to 15% by mass, 3 to 15% by mass, 0.01 to 10% by mass, 0.05 to 10% by mass, 0.1 to 10% by mass, 0.5 to 10% by mass, 1 to 10% by mass, 2 to 10% by mass, 3 to 10% by mass, 0.01 to 5% by mass, 0.05 to 5% by mass, 0.1 to 5% by mass, 0.5 to 5% by mass, 1 to 5% by mass, 2 to 5% by mass or 3 to 5% by mass, relative to the whole amount of the composition.

In the case where the composition of the present invention is prepared into the powdery, granular or tablet-like preparation as one embodiment of the present invention, the content of the oily component can be, for example, 1 to 40% by mass, 3 to 40% by mass, 5 to 40% by mass, 7 to 40% by mass, 10 to 40% by mass, 1 to 35% by mass, 3 to 35% by mass, 5 to 35% by mass, 7 to 35% by mass, 10 to 35% by mass, 1 to 30% by mass, 3 to 30% by mass, 5 to 30% by mass, 7 to 30% by mass or 10 to 30% by mass, relative to the whole amount of the composition.

In the case where the composition of the present invention is prepared into the powdery, granular or tablet-like preparation as one embodiment of the present invention, the content of water in the composition can be, for example, 0.05 to 15% by mass, 0.1 to 15% by mass, 0.5 to 15% by mass, 1 to 15% by mass, 0.05 to 12% by mass, 0.1 to 12% by mass, 0.5 to 12% by mass, 1 to 12% by mass, 0.05 to 10% by mass, 0.1 to 10% by mass, 0.5 to 10% by mass or 1 to 10% by mass, relative to the whole amount of the composition.

In the step of preparing the emulsion composition, a specific gravity modifier may be added to the oily phase, if necessary. One example of the specific gravity modifier includes a synthetic specific gravity modifier such as sucrose acetate isobutyrate ester (SAIB). In the present invention, by using gum ghatti and the modified starch in combination, emulsion particles having small particle diameters can be produced. Therefore, the emulsion composition may be applied to a beverage or the like without using the specific gravity modifier.

In the present invention, the emulsion composition may be produced without using an organic solvent, but is not limited to this embodiment. Examples of the organic solvent which is not needed to be used for the production of the emulsion composition include acetone, cyclohexane, 1-propanol, 2-propanol and dichloromethane.

Use Applications

The emulsion composition or the powdery, granular or tablet-like composition of the present invention can be used in various use applications depending on the types of the oily component used and the like. For example, in the case where the oily component is a colorant, the composition can be used as a colorant preparation. In the case where the oily component is a fragrance or flavor, the composition can be used as a fragrance or flavor preparation. In the case where the oily component is a physiologically active substance, the composition can be used as a physiologically active substance preparation. The emulsion composition or the powdery, granular or tablet-like composition of the present invention can be used as a clouding agent (also referred to as a turbid agent or a cloudy) for imparting a proper level of cloudiness to a water-based medium such as a beverage.

With respect to the emulsion composition or the powdery, granular or tablet-like composition of the present invention, a preferred embodiment is a colorant preparation, and a more preferred embodiment is a carotenoid color preparation.

The content of a colorant in the colorant preparation (including an emulsified carotenoid color preparation) is not particularly limited. For example, the color value ($E^{10\%}_{1\ cm}$) is 100 to 800, preferably 200 to 700, more preferably 300 to 600.

The term "color value ($E^{10\%}_{1\ cm}$)" as used herein is expressed by a numerical value ($E^{10\%}_{1\ cm}$) which is obtained by converting an absorbance at a maximum absorption wavelength in a visible region of a colorant-containing material such as a colorant preparation into an absorbance in a 10-w/v % solution of the colorant-containing material, as is conventionally understood by persons skilled in the art of colorants.

In the present invention, the color value ($E^{10\%}_{1\ cm}$) is a numerical value determined in accordance with "18. Color value measurement method" in Japanese Standards for Food Additives, 9th edition.

1. Water-Based Composition

The present invention also relates to a water-based composition containing the emulsion composition or the powdery, granular or tablet-like composition.

The type of the water-based composition is not particularly limited, and may be, for example, a food or beverage, a cosmetic product, a drug, a quasi-drug, a sanitary household product or a feed, preferably a food or beverage, more preferably a beverage.

The content of the emulsion composition or the powdery, granular or tablet-like composition in the water-based composition may vary depending on the types, intended use or the like of the composition, and can be, for example, 0.001 to 5% by mass or 0.01 to 1% by mass.

The present invention also relates to a food or beverage containing the emulsion composition or the powdery, granular or tablet-like composition.

The type of the food or beverage is not particularly limited. Specific examples of the food or beverage include:

a beverage such as a milk beverage, a lactic acid bacterium beverage, a carbonated beverage, a fruit beverage (e.g., a fruit juice beverage, a fruit juice-containing soft drink, a fruit juice-containing carbonated beverage, a fruit pulp beverage), a vegetable beverage, a vegetable-fruit beverage, an alcohol beverage (e.g., a liqueur), a coffee beverage, a powdery beverage, a sports drink, and a supplemental beverage;

a tea beverage such as a black tea beverage, a green tea beverage and a blended tea (wherein the beverages and tea beverages are included in the definition of "beverage");

a dessert such as pudding (e.g., custard pudding, milk pudding, fruit juice-containing pudding), jelly, bavarois and yogurt;

a cold dessert such as ice cream, iced milk, lacto ice cream and a frozen dessert;

gum such as chewing gum and bubble gum (stick gum, sugar-coated tablet gum);

chocolate such as coated chocolate (e.g., marble chocolate), flavored chocolate (e.g., strawberry-flavored chocolate, blueberry-flavored chocolate, melon-flavored chocolate);

candy such as hard candy (e.g., bonbon, butter scotch, marble) and soft candy (e.g., caramel candy, nougat, gummi candy, marshmallow), sugar-coated candy, drop and toffee);

a confectionary such as cookie and biscuit;

a soup such as a clear soup and a creamed soup;

a liquid seasoning such as a separated dressing, an oil-free dressing, ketchup, basting and a source;

jam such as strawberry jam, blueberry jam, marmalade, apple jam, apricot jam, a preserve and a syrup;

a fruit liquor such as red wine;

a processed fruit product such as a glazed cherry, a glazed apricot, a glazed apple, a glazed strawberry, and a glazed peach;

an agricultural processed product such as pickles;

a processed sea food such as a fish cake; and a processes cereal product such as bread, noodle (including non-fried noodle), steamed bread dough, and rice.

In the examples of the food or beverage, half-finished products, intermediate products and the like of the above-mentioned foods and beverages are also included.

Examples of the "cosmetic product" include a skin lotion, a lip stick, a sunscreen cosmetic and a makeup cosmetic.

Examples of the "drug" include various types of tablets, a capsule preparation, a health drink, a pastille and a gargle.

Examples of the "quasi-drug" include a nutritional aid, various types of supplements, a toothpaste, a mouth refreshing agent, a deodorant agent, a hair restorer, a hair growing agent and a skin moisturizing agent.

Examples of the "sanitary household product" include a soap, a detergent, a shampoo, a hair rinse, a hair treatment, a toothpaste and a bath salt.

Examples of the "feed" include: various types of pet foods such as a cat food and a dog food; and a feed for aquarium fish and a feed for and cultured fish.

Method for Improving Emulsion Stability of Emulsion Composition (Emulsion Stability Improvement Method)

The present invention also relates to a method for improving the emulsion stability of an emulsion composition, having the following embodiment.

A method for improving the emulsion stability of an emulsion composition comprising water, an oily component and gum ghatti, comprising a step of adding a modified starch to the emulsion composition,
wherein the content of gum ghatti is 32% by mass or less, and the content of the modified starch is 500 parts by mass or less relative to 100 parts by mass of the gum ghatti.

The method may be the same as or similar to the embodiment and the preparation method of the emulsion composition of the present invention, and is intended to be understood with reference to the preparation method of the emulsion composition of the present invention.

The method for improving the emulsion stability of an emulsion composition in the present invention includes an embodiment in which the step of adding the modified starch to the emulsion composition is preferably carried out prior to the formation of emulsion particles.

The method for improving the emulsion stability of an emulsion composition in the present invention includes the following preferred embodiment.

A method for improving the emulsion stability of the emulsion composition containing gum ghatti, comprising steps of:
(1) preparing a mixed solution comprising water, an oily component, the gum ghatti and the modified starch; and
(2) homogenizing the mixed solution to prepare an emulsion composition.

EXAMPLES

Hereinbelow, the present invention will be described with reference to examples. However, the present invention is not limited by these examples.

Materials
Gum ghatti: weight average molecular weight 1,120,000 (unless otherwise specified)
Low-molecular-weight gum ghatti: weight average molecular weight 150,000 (unless otherwise specified)
Modified starch: starch sodium octenyl succinate (unless otherwise specified)
SAIB: sucrose acetate isobutyrate ester
The low-molecular-weight gum ghatti was prepared in accordance with the method disclosed in International Publication No. 2018/062554. The weight average molecular weight was measured by a GPC analysis under the following conditions.
Detector: RI
Mobile phase: 100 mM $K_2SO_4$
Flow rate: 1.0 ml/min
Temperature: 40° C.
Column: TSKgel GMPWXL 30 cm (Guard PWXL)
Injection: 100 μl
Pullulan standard: Shodex STANDARD P-82
Method for Preparing Emulsion Compositions
Emulsion compositions were produced in accordance with the formulations shown in tables and by the below-mentioned preparation method.
(Preparation Method)
(Preparation of Oily Phase)
Oily components were mixed together homogeneously. With respect to a formulation containing beta-carotene, oily components were heated and was then warmed (about 160 to 170° C.) appropriately until crystals of beta-carotene were completely dissolved.
(Preparation of Aqueous Phase)
Water, gum ghatti and a modified starch were dissolved by heating (90° C., for 10 minutes), then other water-soluble components were added to the solution, and then the resultant mixture was agitated homogeneously to prepare an aqueous phase.
(Preparation of Emulsion Composition)
The oily phase was added to the aqueous phase, and then the resultant solution was stirred at 3000 rpm for 5 minutes to prepare a preparatory emulsion solution.
The preparatory emulsion solution was homogenized using a high-pressure homogenizer (15MR-8TA, manufactured by MANTON-GAULIN) (conditions: 560 kg/cm$^2$, 5 passes).
Evaluation Methods
Each of the emulsion compositions was evaluated with respect to the following items.
D50 (μm): median diameter (μm)
1.3 μm↑: frequency (%) of particle diameter of 1.3 μm or more.
For the median diameter or the frequency of particle diameter, the particle size distribution of each of the emulsion compositions was measured under the following conditions.
<Conditions>
Particle size distribution measurement device: Microtrac MT3000EX-II (MicrotracBEL Corporation)
Measurement method: refraction index: 1.81, measurement range: 0.021 to 2000 μm, particle size distribution: volume-based
In the results, "N.D" indicates that the measurement was not carried out.

Experiment Example 1: Emulsion Compositions

Emulsion compositions were produced in accordance with the formulations shown in Table 1.
Preparatory emulsion compositions, emulsion compositions, and the emulsion compositions after being stored at 60° C. for 7 days were evaluated with respect to the items "D50 (μm)" and "1.3 μm↑". The results are shown in Table 1.

TABLE 1

| FORMULATION OF EMULSION | | EXAMPLE | | | | | COMPARATIVE EXAMPLE | | | |
|---|---|---|---|---|---|---|---|---|---|---|
| | COMPOSITION (% by mass) | 1-1 | 1-2 | 1-3 | 1-4 | 1-5 | 1-1 | 1-2 | 1-3 | 1-4 |
| OILY PHASE | BETA-CAROTENE | 2.35 | 2.35 | 3.53 | 1.18 | 5.23 | 2.35 | 2.35 | 2.35 | 2.35 |
| | dl-α-TOCOPHEROL | 0.1 | 0.1 | 0.1 | 0.1 | 0.1 | 0.1 | 0.1 | 0.1 | 0.1 |
| | MEDIUM-CHAIN FATTY ACID TRIGLYCERIDE | 11.05 | 11.05 | 9.87 | 3.72 | 14.67 | 11.05 | 11.05 | 11.05 | 11.05 |
| | TOTAL OF OILY PHASE | 13.5 | 13.5 | 13.5 | 5.0 | 20.0 | 13.5 | 13.5 | 13.5 | 13.5 |
| AQUEOUS PHASE | Gum ghatti | 6.0 | 6.0 | 6.0 | 6.0 | 6.0 | 6.0 | 6.0 | 6.0 | 6.0 |
| | Modified starch | 0.75 | 1.5 | 0.75 | 0.75 | 0.75 | — | — | — | — |
| | SUCROSE ESTER OF | — | — | — | — | — | — | 0.5 | 1.5 | 3 |

TABLE 1-continued

| FORMULATION OF EMULSION | EXAMPLE | | | | | COMPARATIVE EXAMPLE | | | |
|---|---|---|---|---|---|---|---|---|---|
| COMPOSITION (% by mass) | 1-1 | 1-2 | 1-3 | 1-4 | 1-5 | 1-1 | 1-2 | 1-3 | 1-4 |
| FATTY ACID GLYCERIN | 38.3 | 38.3 | 38.3 | 41.25 | 34.8 | 38.3 | 38.3 | 38.3 | 38.3 |
| LACTIC ACID (50% AQUEOUS SOLUTION) | 1.2 | 1.2 | 1.2 | 2.0 | 1.2 | 1.2 | 1.2 | 1.2 | 1.2 |
| CITRIC ACID (ANHYDROUS) | 0.2 | 0.2 | 0.2 | 0.2 | 0.2 | 0.2 | 0.2 | 0.2 | 0.2 |
| L-ASCORBIC ACID | 0.5 | 0.5 | 0.5 | 0.5 | 0.5 | 0.5 | 0.5 | 0.5 | 0.5 |
| ION-EXCHANGE WATER | 39.55 | 38.8 | 39.55 | 44.3 | 36.55 | 40.3 | 39.8 | 38.8 | 37.3 |
| TOTAL OF AQUEOUS PHASE | 86.5 | 86.5 | 86.5 | 95.0 | 80.0 | 86.5 | 86.5 | 86.5 | 86.5 |
| CONTENT OF MODIFIED STARCH RELATIVE TO 100 PARTS BY MASS OF GUM GHATTI (PART(S) BY MASS) | 12.5 | 25 | 12.5 | 12.5 | 12.5 | 0 | 0 | 0 | 0 |
| PREPARATORY EMULSION SOLUTION, D50 (μm) | 5.37 | 4.10 | 5.42 | 5.11 | 5.38 | 11.38 | 4.81 | OIL/WATER SEPARATION WAS OBSERVED | |
| PREPARATORY EMULSION SOLUTION, 1.3 μm↑ (%) | 99 | 99 | 100 | 100 | 100 | 100 | 98 | | |
| EMULSION COMPOSITION, D50 (μm) | 0.32 | 0.21 | 0.23 | 0.13 | 0.42 | 0.57 | 0.71 | HOMOGENIZATION WAS IMPOSSIBLE | |
| EMULSION COMPOSITION, 1.3 μm↑ (%) | 0 | 0 | 0 | 0 | 0 | 2 | 19 | | |
| STORED AT 60° C. FOR 7 DAYS, D50 (μm) | 0.33 | 0.21 | 0.24 | 0.14 | 0.42 | 0.58 | OIL/WATER SEPARATION WAS OBSERVED | OIL/WATER SEPARATION WAS OBSERVED | |
| STORED AT 60° C. FOR 7 DAYS, 1.3 μm↑ (%) | 0 | 0 | 0 | 0 | 0 | 3 | | | |

As shown in Table 1, it was demonstrated that, when gum ghatti and a modified starch were used in combination, an emulsion composition having smaller emulsion particle diameters compared with a case where gum ghatti was used singly could be prepared (Examples 1-1 to 1-5). Each of the emulsion compositions retained smaller emulsion particle diameters after being stored at 60° C. for 7 days. In these results, the same tendency was shown when the content of the oily components in the oily phase was large (Examples 1-1 to 1-5). In contrast, when gum ghatti and a sucrose ester of a fatty acid were used in combination, the emulsion particle diameters were increased compared with a case where gum ghatti was used singly, and the emulsion particles could not be retained after 7 days at 60° C. and phase separation occurred (Comparative Example 1-2). In Comparative Examples 1-3 and 1-4 in each of which the content of a sucrose ester of a fatty acid to be used in combination with gum ghatti was increased, an emulsion composition could not be prepared. It was assumed that a sucrose fatty acid ester inhibited the emulsification of gum ghatti.

Experiment Example 2: Emulsion Compositions

Emulsion compositions were produced in accordance with the formulations shown in Table 2. The emulsion compositions were prepared in the same manner as in the above-mentioned "method for preparing emulsion compositions", except that the formulations of an oily phase and an aqueous phase were altered.

Preparatory emulsion compositions, emulsion compositions, and the emulsion compositions after being stored at 60° C. for 7 days were evaluated with respect to the items "D50 (μm)" and "1.3 μm↑". The results are shown in Table 2.

TABLE 2

| FORMULATION OF EMULSION | | EXAMPLE | | COMPARATIVE EXAMPLE | | |
|---|---|---|---|---|---|---|
| COMPOSITION (% by mass) | | 2-1 | 2-2 | 2-1 | 2-2 | 2-3 |
| OILY PHASE | BETA-CAROTENE | 5.88 | 5.88 | 5.88 | 5.88 | 5.88 |
| | dl-α-TOCOPHEROL | 0.1 | 0.1 | 0.1 | 0.1 | 0.1 |
| | MEDIUM-CHAIN FATTY ACID TRIGLYCERIDE | 16.52 | 16.52 | 16.52 | 16.52 | 16.52 |
| | TOTAL OF OILY PHASE | 22.50 | 22.50 | 22.50 | 22.50 | 22.50 |
| AQUEOUS PHASE | LOW-MOLECULAR-WEIGHT GUM GHATTI | 8 | 4.5 | 9 | 1 | — |
| | Modified starch | 1 | 4.5 | — | 8 | 9 |
| | GLYCERIN | 31.5 | 32 | 32 | 32 | 34 |
| | LACTIC ACID (50% AQUEOUS SOLUTION) | 0.8 | 0.5 | 0.5 | 0.5 | 0.5 |
| | CITRIC ACID (ANHYDROUS) | 0.2 | — | — | — | — |
| | L-ASCORBIC ACID | 0.5 | 0.5 | 0.5 | 0.5 | 0.5 |
| | ION-EXCHANGE WATER | 35.5 | 35.5 | 35.5 | 35.5 | 33.5 |
| | TOTAL OF AQUEOUS PHASE | 77.5 | 77.5 | 77.5 | 77.5 | 77.5 |

TABLE 2-continued

| FORMULATION OF EMULSION | EXAMPLE | | COMPARATIVE EXAMPLE | | |
|---|---|---|---|---|---|
| COMPOSITION (% by mass) | 2-1 | 2-2 | 2-1 | 2-2 | 2-3 |
| CONTENT OF MODIFIED STARCH RELATIVE TO 100 PARTS BY MASS OF LOW-MOLECULAR-WEIGHT GUM GHATTI (PART(S) BY MASS) | 12.5 | 100 | 0 | 800 | — |
| PREPARATORY EMULSION SOLUTION, D50 (μm) | 7.68 | 8.87 | 6.55 | 7.32 | 11.63 |
| PREPARATORY EMULSION SOLUTION, 1.3 μm↑ (%) | 100 | 100 | 100 | 99 | 100 |
| EMULSION COMPOSITION, D50 (μm) | 0.25 | 0.15 | 0.43 | 0.14 | 0.16 |
| EMULSION COMPOSITION, 1.3 μm↑ (%) | 0 | 0 | 0 | 0 | 0 |
| STORED AT 60° C. FOR 7 DAYS, D50 (μm) | 0.26 | 0.42 | 0.44 | OIL/WATER SEPARATION WAS OBSERVED | OIL/WATER SEPARATION WAS OBSERVED |
| STORED AT 60° C. FOR 7 DAYS, 1.3 μm↑ (%) | 0 | 12 | 0 | | |

As shown in Table 2, it was demonstrated that, when low-molecular-weight gum ghatti and a modified starch were used in combination, an emulsion composition having smaller emulsion particle diameters compared with a case where low-molecular-weight gum ghatti was used singly could be prepared (Examples 2-1 to 2-2). In contrast, in each of an emulsion composition of Comparative Example 2-2 in which the content of a modified starch relative to 100 parts by mass of low-molecular-weight gum ghatti was 800 parts by mass and an emulsion composition of Comparative Example 2-3 in which a modified starch was used singly, emulsion particles showed smaller particle diameters during the preparation of the emulsion composition, but the emulsion particles could not be retained anymore after 7 days at 60° C. and phase separation occurred.

Experiment Example 3: Emulsion Compositions

Emulsion compositions were produced in accordance with the formulations shown in Table 3. The emulsion compositions were prepared in the same manner as in the above-mentioned "method for preparing emulsion compositions", except that the formulations of an oily phase and an aqueous phase were altered.

Emulsion compositions and the emulsion compositions stored at 60° C. for 7 days were evaluated with respect to the items "D50 (μm)" and "1.3 μm↑". The results are shown in Table 3.

TABLE 3

| FORMULATION OF EMULSION | | EXAMPLE | COMPARATIVE EXAMPLE | | |
|---|---|---|---|---|---|
| COMPOSITION (% by mass) | | 3-1 | 3-1 | 3-2 | 3-3 |
| OILY PHASE | MEDIUM-CHAIN FATTY ACID TRIGLYCERIDE | 25.5 | 25.5 | 25.5 | 25.5 |
| | TOTAL OF OILY PHASE | 25.5 | 25.5 | 25.5 | 25.5 |
| AQUEOUS PHASE | Gum ghatti | 5.5 | 5.5 | — | 5.5 |
| | Modified starch | 2 | — | — | — |
| | SUCROSE ESTER OF FATTY ACID | — | — | 2 | 2 |
| | GLYCERIN | 34.5 | 35.5 | 38 | 34.5 |
| | LACTIC ACID (50% AQUEOUS SOLUTION) | 0.5 | 0.5 | — | 0.5 |
| | CITRIC ACID (ANHYDROUS) | 0.1 | 0.1 | — | 0.1 |
| | ION-EXCHANGE WATER | 31.9 | 32.9 | 34.5 | 31.9 |
| | TOTAL OF AQUEOUS PHASE | 74.5 | 74.5 | 74.5 | 74.5 |
| | CONTENT OF MODIFIED STARCH RELATIVE TO 100 PARTS BY MASS OF GUM GHATTI (PART(S) BY MASS) | 36.36 | 0 | — | 0 |
| | EMULSION COMPOSITION, D50 (μm) | 0.59 | 2.06 | 0.14 | 0.15 |
| | EMULSION COMPOSITION, 1.3 μm↑ (%) | 2 | 99 | 0 | 0 |
| | STORED AT 60° C. FOR 7 DAYS, D50 (μm) | N.D | N.D | OIL/WATER SEPARATION WAS OBSERVED | N.D |
| | STORED AT 60° C. FOR 7 DAYS, 1.3 μm↑ (%) | N.D | N.D | | N.D |

As shown in Table 3, it was demonstrated that, when gum ghatti and a modified starch were used in combination, an emulsion composition having significantly smaller emulsion particle diameters compared with a case where gum ghatti was used singly (Comparative Example 3-1) could be prepared (Example 3-1). In the emulsion composition of Comparative Example 3-2 in which a sucrose ester of a fatty acid was used singly as an emulsifying agent in place of gum ghatti, although the emulsion particle diameters immediately after the preparation of the emulsion composition were as small as 0.14 μm, the emulsion composition underwent phase separation after being stored at 60° C. for 7 days. In the emulsion composition of Comparative Example 3-3 in which gum ghatti and a sucrose ester of a fatty acid were used in combination, although the measurement value of each of emulsion particle diameters was as small as 0.15 μm, the particle size distribution was non-uniform as shown in FIG. 1. It was assumed that the emulsion composition was not suitable for long-term storage. The diagrams of particle size distributions shown in FIG. 1 were produced using a software included in the particle size distribution measurement device Microtrac MT3000EX-II (MicrotracBEL Corporation).

Experiment Example 4: Emulsion Compositions

Emulsion compositions were produced in accordance with the formulations shown in Table 4. The emulsion compositions were prepared in the same manner as in the above-mentioned "method for preparing emulsion compositions", except that the formulations of an oily phase and an aqueous phase were altered.

Emulsion compositions and the emulsion compositions stored at 60° C. for 7 days were evaluated with respect to the items "D50 (μm)" and "1.3 μm↑". The results are shown in Table 4.

As shown in Table 4, it was demonstrated that, when low-molecular-weight gum ghatti and a modified starch were used in combination, an emulsion composition having significantly smaller emulsion particle diameters compared with a case where low-molecular-weight gum ghatti was used singly (Comparative Example 4-1) could be prepared (Examples 4-1 and 4-2). The emulsion composition of Example 4-2 was subjected to a storage test at 60° C. for 7 days. It was demonstrated that the emulsion particle diameters after the storage were retained at a level of as small as 0.82 μm.

Experiment Example 5: Emulsion Compositions

Emulsion compositions were produced in accordance with the formulations shown in Table 5. The emulsion compositions were prepared in the same manner as in the above-mentioned "method for preparing emulsion compositions", except that the formulations of an oily phase and an aqueous phase were altered.

Emulsion compositions and the emulsion compositions stored at 60° C. for 7 days were evaluated with respect to the items "D50 (μm)" and "1.3 μm↑". The results are shown in Table 5.

TABLE 4

| FORMULATION OF EMULSION | | EXAMPLE | | COMPARATIVE EXAMPLE |
|---|---|---|---|---|
| COMPOSITION (% by mass) | | 4-1 | 4-2 | 4-1 |
| OILY PHASE | BETA-CAROTENE | 11.76 | 11.76 | 11.76 |
| | dl-α-TOCOPHEROL | 1 | 1 | 1 |
| | MEDIUM-CHAIN FATTY ACID TRIGLYCERIDE | 34.24 | 27.24 | 34.24 |
| | TOTAL OF OILY PHASE | 47 | 40 | 47 |
| AQUEOUS PHASE | LOW-MOLECULAR-WEIGHT GUM GHATTI | 1.5 | 3 | 1 |
| | Modified starch | 0.25 | 0.5 | — |
| | GLYCERIN | 22.5 | 26 | 22 |
| | LACTIC ACID (50% AQUEOUS SOLUTION) | 1 | 0.5 | 1 |
| | CITRIC ACID (ANHYDROUS) | 0.5 | 0.5 | 0.5 |
| | ION-EXCHANGE WATER | 27.25 | 29.5 | 28.5 |
| | TOTAL OF AQUEOUS PHASE | 53 | 60 | 53 |
| | CONTENT OF MODIFIED STARCH RELATIVE TO 100 PARTS BY MASS OF LOW-MOLECULAR-WEIGHT GUM GHATTI (PART(S) BY MASS) | 16.67 | 16.67 | 0 |
| | EMULSION COMPOSITION, D50 (μm) | 1.35 | 0.76 | 3.35 |
| | EMULSION COMPOSITION, 1.3 μm↑ (%) | 58 | 13 | 100 |
| | STORED AT 60° C. FOR 7 DAYS, D50 (μm) | N.D | 0.82 | N.D |
| | STORED AT 60° C. FOR 7 DAYS, 1.3 μm↑ (%) | N.D | 18 | N.D |

TABLE 5

| FORMULATION OF EMULSION | | EXAMPLE | | | | |
|---|---|---|---|---|---|---|
| | COMPOSITION (% by mass) | 5-1 | 5-2 | 5-3 | 5-4 | 5-5 |
| OILY PHASE | BETA-CAROTENE | 11.76 | 11.76 | 11.76 | 11.76 | 11.76 |
| | dl-α-TOCOPHEROL | 1 | 1 | 1 | 1 | 1 |
| | MEDIUM-CHAIN FATTY ACID TRIGLYCERIDE | 13.24 | 13.24 | 13.24 | 13.24 | 13.24 |
| | TOTAL OF OILY PHASE | 26 | 26 | 26 | 26 | 26 |
| AQUEOUS PHASE | LOW-MOLECULAR-WELGHT GUM GHATTI | 8 | 8 | 6 | 6 | 4.5 |
| | Modified starch | 1 | 0.5 | 0.5 | 3 | 4.5 |
| | GLYCERIN | 31 | 31.1 | 32.1 | 30 | 31 |
| | LACTIC ACID (50% AQUEOUS SOLUTION) | 0.5 | 0.5 | 0.5 | 0.5 | 0.5 |
| | L-ASCORBIC ACID | 0.5 | 0.5 | 0.5 | 0.5 | 0.5 |
| | ION-EXCHANGE WATER | 33 | 33.4 | 34.4 | 34 | 33 |
| | TOTAL OF AQUEOUS PHASE | 74 | 74 | 74 | 74 | 74 |
| | CONTENT OF MODIFIED STARCH RELATIVE TO 100 PARTS BY MASS OF LOW-MOLECULAR-WELGHT GUM GHATTI (PART(S) BY MASS) | 12.5 | 6.25 | 8.33 | 50 | 100 |
| | EMULSION COMPOSITION, D50 (μm) | 0.26 | 0.26 | 0.28 | 0.18 | 0.18 |
| | EMULSION COMPOSITION, 1.3 μm↑ (%) | 0 | 0 | 0 | 0 | 0 |
| | STORED AT 60° C. FOR 7 DAYS, D50 (μm) | 0.28 | 0.28 | 0.30 | 0.46 | 0.44 |
| | STORED AT 60° C. FOR 7 DAYS, 1.3 μm↑ (%) | 0 | 2 | 4 | 16 | 15 |

As shown in Table 5, it was demonstrated that, when low-molecular-weight gum ghatti and a modified starch were used in combination, an emulsion composition having emulsion particle diameters around 0.2 μm could be prepared (Examples 5-1 to 5-5).

Experiment Example 6: Emulsion Compositions

Emulsion compositions were produced in accordance with the formulations shown in Table 6. The emulsion compositions were prepared in the same manner as in the above-mentioned "method for preparing emulsion compositions", except that the formulations of an oily phase and an aqueous phase were altered.

Emulsion compositions and the emulsion compositions stored at 60° C. for 7 days were evaluated with respect to the items "D50 (μm)" and "1.3 μm↑". The results are shown in Table 6.

As shown in Table 6, it was demonstrated that, when gum ghatti and a modified starch were used in combination, an emulsion composition having smaller emulsion particle diameters compared with a case where gum ghatti was used singly could be prepared regardless the presence or absence of SAIB (sucrose acetate isobutyrate ester). In the case where SAIB was not used, the emulsion particle diameters tended to be increased compared with a case where SAIB was used. Even in this case, it was demonstrated that, by using gum ghatti and a modified starch in combination, an emulsion composition having smaller emulsion particle diameters could be prepared.

Experiment Example 7: Storage Test

Each of the emulsion compositions prepared in Examples 1-1, 1-3 and 2-1 was subjected to a storage test when each of the emulsion compositions was diluted.

TABLE 6

| FORMULATION OF EMULSION | | EXAMPLE | | COMPARATIVE EXAMPLE | |
|---|---|---|---|---|---|
| | COMPOSITION (% by mass) | 6-1 | 6-2 | 6-1 | 6-2 |
| OILY PHASE | SAIB | — | 10 | — | 10 |
| | MEDIUM-CHAIN FATTY ACID TRIGLYCERIDE | 13.5 | 3.5 | 13.5 | 3.5 |
| | TOTAL OF OILY PHASE | 13.5 | 13.5 | 13.5 | 13.5 |
| AQUEOUS PHASE | Gum ghatti | 6 | 6 | 6 | 6 |
| | Modified starch | 0.75 | 0.75 | — | — |
| | GLYCERIN | 38.3 | 38.3 | 38.3 | 38.3 |
| | LACTIC ACID (50% AQUEOUS SOLUTION) | 1.2 | 1.2 | 1.2 | 1.2 |
| | CITRIC ACID (ANHYDROUS) | 0.2 | 0.2 | 0.2 | 0.2 |
| | L-ASCORBIC ACID | 0.5 | 0.5 | 0.5 | 0.5 |
| | ION-EXCHANGE WATER | 39.55 | 39.55 | 40.3 | 40.3 |
| | TOTAL OF AQUEOUS PHASE | 86.5 | 86.5 | 86.5 | 86.5 |
| | CONTENT OF MODIFIED STARCH RELATIVE TO 100 PARTS BY MASS OF GUM GHATTI (PART(S) BY MASS) | 12.5 | 12.5 | 0 | 0 |
| | PREPARATORY EMULSION SOLUTION, D50 (μm) | 4.55 | 14.39 | 4.8 | 15.93 |
| | PREPARATORY EMULSION SOLUTION, 1.3 μm↑ (%) | 100 | 100 | 100 | 100 |
| | Emulsion composition, D50 (μm) | 0.53 | 0.18 | 0.82 | 0.26 |
| | EMULSION COMPOSITION, 1.3 μm↑ (%) | 2 | 0 | 11 | 0 |

Each of the emulsion compositions was diluted with ion-exchange water in such a manner that the carotene concentration in the diluted solution became 100 ppm, and the diluted solution was allowed to stand overnight. In any one of the diluted solutions, the precipitation of carotene crystals was not observed.

Experiment Example 8: Aeration Test

Each of the emulsion compositions prepared in Examples 2-1 and 2-2 and Comparative Example 2-3 was subjected to an aeration test.

Test solutions were prepared in accordance with the formulation shown in Table 7, and the prepared test solutions were subjected to an aeration test under the following conditions. The results are shown in Table 8 and FIG. 2.

(Conditions for Aeration Test)
Container: a 2-L stainless mug
Liquid volume: 2000 mL
Warming: warm to 90° C.
Stirring: 1000 rpm (a three-bladed stirrer)
Air flow amount: 1000 mL/min
Sampling: at time of start, at time at which temperature reached 90° C. (100 mL for each)

TABLE 7

| | FORMULATION OF TEST SOLUTION | % BY MASS |
|---|---|---|
| SYRUP PART | FRUCTOSE-GLUCOSE SYRUP (BRIX: 75) | 13.33 |
| | CITRIC ACID (ANHYDROUS) | 0.2 |
| | TRISODIUM CITRATE | 0.12 |
| | ASCORBIC ACID | 0.02 |
| | 10% DILUTED SOLUTION OF EACH EMULSION COMPOSITION | 0.2 |
| | ION-EXCHANGE WATER | 11.13 |
| | TOTAL OF SYRUP PART | 25 |
| | ION-EXCHANGE WATER | 75 |

TABLE 8

| EMULSION COMPOSITION USED | | D50 (μm) | 1.3 μm↑ (%) |
|---|---|---|---|
| EXAMPLE 2-1 | TIME OF START | 0.28 | 0 |
| | TIME AT WHICH TEMPERATURE REACHED 90° C. | 0.29 | 0 |
| EXAMPLE 2-2 | TIME OF START | 0.15 | 0 |
| | TIME AT WHICH TEMPERATURE REACHED 90° C. | 0.31 | 0 |
| COMPARATIVE EXAMPLE 2-3 | TIME OF START | 0.11 | 0 |
| | TIME AT WHICH TEMPERATURE REACHED 90° C. | 10.5 | 87 |

The emulsion compositions of Examples 2-1 and 2-2 were examples in each of which low-molecular-weight gum ghatti and a modified starch were used in combination. It was demonstrated that, in spite of the severe test conditions, i.e., warming and aeration under stirring, each of the emulsion compositions of Examples 2-1 and 2-2 retained small emulsion particle diameters and showed extremely high storage stability (Table 8, FIG. 2).

Figure 2:
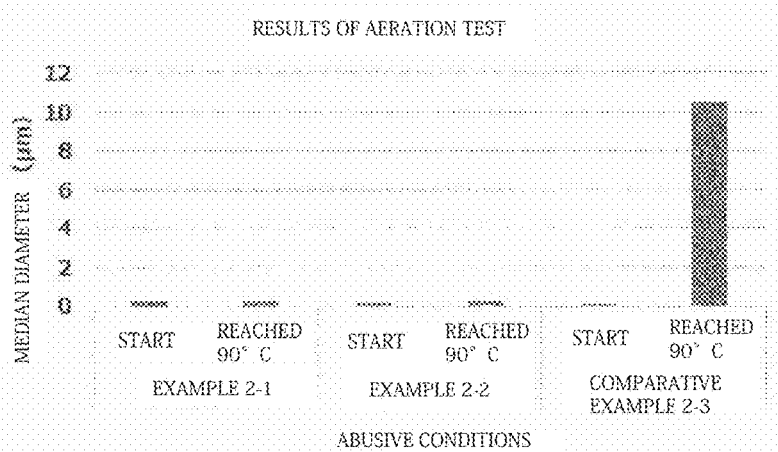
FIG. 2 illustrates graphs showing the storage stability of emulsion compositions in an aeration test in Experiment Example 8.

In contrast, in the emulsion composition of Comparative Example 2-3 in which a modified starch was used singly, the emulsion particle diameters at a time point at which the temperature reached 90° C. were enlarged to 10.5 μm (Table 8, FIG. 2).

Experiment Example 9: Beverage Test

Beverages having different Brix values were prepared in accordance with the formulations shown in Table 9.

(Method for Producing Beverages)

A 10% dilution solution of a sample and supplemental ion-exchange water were added to a standard Brix solution to prepare a syrup. The syrup was mixed with ion-exchange water, the resultant solution was sterilized by heating to 93° C., then vaporized water was made up, and then the solution was hot-packed in a 200-mL plastic bottle. The bottle was stored in a thermostatic bath at 40° C. for 2 months, and the solution was evaluated with respect to the items "D50 (μm)" and "1.3 μm↑" after the storage. The results are shown in Table 9.

TABLE 9

| FORMULATION OF BEVERAGE (% BY MASS) | | EMULSION COMPOSITION USED | | | | | |
|---|---|---|---|---|---|---|---|
| | | EXAMPLE 1-3 | | | EXAMPLE 2-1 | | |
| | | BRIX (DEGREE) | | | | | |
| | | 0 | 5 | 10 | 0 | 5 | 10 |
| SYRUP PART | FRUCTOSE-GLUCOSE SYRUP (BRIX: 75) | — | 6.67 | 13.33 | — | 6.67 | 13.33 |
| | CITRIC ACID (ANHYDROUS) | 0.2 | 0.2 | 0.2 | 0.2 | 0.2 | 0.2 |
| | TRISODIUM CITRATE | 0.12 | 0.12 | 0.12 | 0.12 | 0.12 | 0.12 |
| | ASCORBIC ACID | 0.02 | 0.02 | 0.02 | 0.02 | 0.02 | 0.02 |
| | 10% DILUTED SOLUTION OF EACH EMULSION COMPOSITION | 0.33 | 0.33 | 0.33 | 0.2 | 0.2 | 0.2 |
| | ION-EXCHANGE WATER | 24.33 | 17.66 | 11 | 24.46 | 17.79 | 11.13 |
| | TOTAL OF SYRUP PART | 25 | 25 | 25 | 25 | 25 | 25 |
| | ION-EXCHANGE WATER | 75 | 75 | 75 | 75 | 75 | 75 |
| STORED AT 40° C. FOR 2 MONTHS, D50 (μm) | | 0.25 | 0.26 | 0.26 | 0.28 | 0.28 | 0.28 |
| STORED AT 40° C. FOR 2 MONTHS, 1.3 μm↑ (%) | | 0 | 0 | 0 | 0 | 0 | 0 |

As shown in Table 9, each of the beverages prepared using the emulsion compositions of Examples 1-3 and 2-1 showed small emulsion particle diameters after being stored at 40° C. for 2 months at all of the Brix values. From the results, it was demonstrated that the emulsion compositions of the present invention showed excellent long-term stability in beverages.

Experiment Example 10: Example of Coloration (Soft Drink Model System)

Colored samples of soft drink model systems were prepared using the emulsion composition of Example 2-1.

Figure 3:
FIG. 3 is a photographic image showing the results of the coloration of soft drink models with emulsion compositions in Experiment Example 10.

In order to prepare soft drink model systems, the emulsion composition of Example 2-1 was added to ion-exchange water in such a manner that the concentration of beta-carotene became 5 ppm, 10 ppm and 20 ppm. The results are shown in FIG. 3. All of the soft drink model systems were colored uniformly.

Experiment Example 11: Example of Coloration (Milk Beverage Model System)

Colored samples of milk beverage model systems were prepared using the emulsion composition of Example 2-1.

Figure 4:
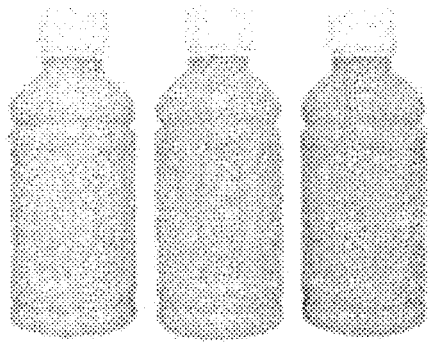
FIG. 4 is a photographic image showing the results of the coloration of milk beverage models with emulsion compositions in Experiment Example 11.

In order to prepare milk beverage model systems, the emulsion composition of Example 2-1 was added to a mixed solution composed of 30% of milk and 70% of exchange water in such a manner that the concentration of beta-carotene became 5 ppm, 10 ppm and 20 ppm. The results are shown in FIG. 4. All of the soft drink model systems were colored uniformly.

Experiment Example 12: Coloring Example (Pudding)

Colored samples of pudding were prepared in accordance with the formulations shown in Table 10.

(Production Method)

A powdery mixture composed of components 5 to 10 shown in Table 10 was added to components 1 to 4 shown in Table 10 while stirring the components 1 to 4, and the resultant mixture was dissolved while heating and stirring at 90° C. for 10 minutes. The resultant product was homogenized (a high-pressure homogenizer, pressure: 100 kg/cm²) and was then dispensed into portions each having a predetermined volume, and then components 11 to 13 were added to each of the portions. The resultant portions were respectively filled in containers and were then solidified by cooling to prepare pudding samples.

TABLE 10

| FORMULATION (% BY MASS) | CONCENTRATION OF BETA-CAROTENE | | |
|---|---|---|---|
| | 5 ppm | 10 ppm | 20 ppm |
| 1. ION-EXCHANGE WATER | 66.27 | 66.17 | 66.17 |
| 2. WHOLE FAT SWEETENED CONDENSED MILK | 18 | 18 | 18 |
| 3. MILK | 6 | 6 | 6 |
| 4. PALM OIL | 6 | 6 | 6 |
| 5. GRANULATED SUGAR | 2.5 | 2.5 | 2.5 |
| 6. GELLING AGENT ("GEL UP" (REGISTERED TRADENAME) PI-800) | 0.6 | 0.6 | 0.6 |
| 7. CORN STARCH | 0.15 | 0.15 | 0.15 |
| 8. TRISODIUM CITRATE | 0.1 | 0.1 | 0.1 |
| 9. COMMON SALT | 0.08 | 0.08 | 0.08 |
| 10. EMULSIFYING AGENT ("HOMOGEN" (REGISTERED TRADENAME, DM-S) | 0.1 | 0.1 | 0.1 |

TABLE 10-continued

| FORMULATION (% BY MASS) | CONCENTRATION OF BETA-CAROTENE | | |
|---|---|---|---|
| | 5 ppm | 10 ppm | 20 ppm |
| 11. 10% AQUEOUS SOLUTION OF EMULSION COMPOSITION OF EXAMPLE 2-1 | 0.1 | 0.2 | — |
| 12. 20% AQUEOUS SOLUTION OF EMULSION COMPOSITION OF EXAMPLE 2-1 | — | — | 0.2 |
| 13. FLAVOR (PUDDLNG FLAVOR No. 20-5049) | 0.1 | 0.1 | 0.1 |
| TOTAL | 100 | 100 | 100 |

Figure 5:
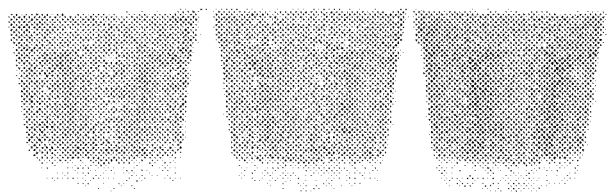
FIG. 5 is a photographic image showing the results of the coloration of pudding with emulsion compositions in Experiment Example 12.

The results are shown in FIG. 5. As shown in FIG. 5, when the emulsion composition of the present invention was used, uniformly colored pudding could be prepared.

Experiment Example 13: Coloring Example (Jelly)

Colored sample of jelly (orange jelly) were prepared in accordance with the formulations shown in Table 11.

(Production Method)

A powdery mixture composed of components 1, 4 and 7 shown in Table 11 were added to components 2 and 12 shown in Table 11 with stirring, and the resultant mixture was dissolved with stirring at 80° C. for 10 minutes. Components 3, 5, 6 and 8 to 11 were added to and mixed with the resultant product, and the mixed solution was filled in containers and was the sterilized at 85° C. for 30 minutes to prepare jelly samples.

TABLE 11

| FORMULATION (% BY MASS) | CONCENTRATION OF BETA-CAROTENE | | |
|---|---|---|---|
| | 5 ppm | 10 ppm | 20 ppm |
| 1. SUGAR | 5 | 5 | 5 |
| 2. FRUCTOSE-GLUCOSE SYRUP (BRIX: 75 DEGREES) | 15 | 15 | 15 |
| 3. CLEAR CONCENTRATED FRUIT JUICE OF CITRUS FRUIT (BRIX: 53 DEGREES) | 2 | 2 | 2 |
| 4. TRISODIUM CITRATE | 0.1 | 0.1 | 0.1 |
| 5. CITRIC ACID (ANHYDROUS) | 0.2 | 0.2 | 0.2 |
| 6. L-ASCORBIC ACID (CRYSTAL) | 0.05 | 0.05 | 0.05 |
| 7. GELLING AGENT ("GEL UP" (REGISTERED TRADENAME) WM-100(F)) | 0.8 | 0.8 | 0.8 |
| 8. 10% AQUEOUS SOLUTION OF EMULSION COMPOSITION OF EXAMPLE 2-1 | 0.1 | — | — |
| 9. 20% AQUEOUS SOLUTION OF EMULSION COMPOSITION OF EXAMPLE 2-1 | — | 0.2 | 0.2 |
| 10. FLAVOR (ORANGE MODIFIER NO. 1(P)) | 0.15 | 0.15 | 0.15 |
| 11. FLAVOR (SUN AROMA (REGISTERED TRADENAME) FAM NO. 9602(N)) | 0.02 | 0.02 | 0.02 |
| 12. ION-EXCHANGE WATER | 76.58 | 76.48 | 76.48 |
| TOTAL | 100 | 100 | 100 |

Figure 6:
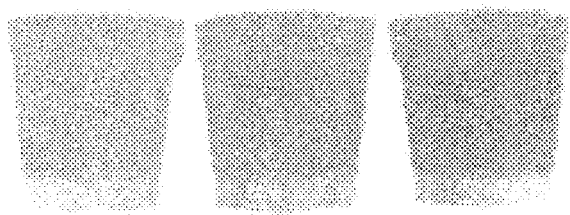
FIG. 6 is a photographic image showing the results of the coloration of jelly with emulsion compositions in Experiment Example 13.

The results are shown in FIG. 6. As shown in FIG. 6, when the emulsion composition of the present invention was used, uniformly colored jelly could be prepared.

Experiment Example 14: Colored Example (Non-Fried Noodle)

Colored samples of a non-fried noodle were prepared in accordance with the formulations shown in Table 12.

(Production Method)

An instant noodle (a non-fried noodle) was prepared in the conventional manner.

Components 3 to 7 shown in Table 12 were dissolved in component 8 shown in Table 12, and the resultant solution was added to a mixture of components 1 and 2 shown in Table 12. The resultant product was kneaded with a mixer for 4 minutes to prepare a dough. The dough was folded and then stretched with a noodle making machine to produce noodle strips. The noodle was steamed for 6 minutes. After 3 minutes, then a lid was removed, and then water was sprayed over the noodle. The noodle was loosened rapidly to cool the noodle properly.

The noodles were placed in a molding frame, and were then dried at 90° C. for 30 minutes.

TABLE 12

| FORMULATION (PART(S) BY MASS) | CONCENTRATION OF BETA-CAROTENE | | |
|---|---|---|---|
| | 5 ppm | 20 ppm | 80 ppm |
| 1. ALL-PURPOSE FLOUR FOR NOODLES | 80 | 80 | 80 |
| 2. POTATO STARCH | 20 | 20 | 20 |
| 3. COMMON SALT | 1 | 1 | 1 |
| 4. SODIUM CARBONATE | 0.27 | 0.27 | 0.27 |
| 5. POTASSIUM CARBONATE | 0.27 | 0.27 | 0.27 |
| 6. SODIUM DIHYDROGEN PHOSPHATE | 0.06 | 0.06 | 0.06 |
| 7. 10% AQUEOUS SOLUTION OF EMULSION COMPOSITION OF EXAMPLE 2-1 | 0.1 | 0.4 | 1.6 |
| 8. WATER | 35.4 | 35.1 | 33.9 |
| TOTAL | 137.1 | 137.1 | 137.1 |

Figure 7:
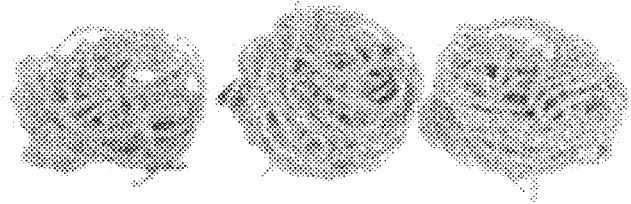
FIG. 7 is a photographic image showing the results of the coloration of non-fried noodles with emulsion compositions in Experiment Example 14.

The results are shown in FIG. 7. As shown in FIG. 7, when the emulsion composition of the present invention was used, a uniformly colored non-fried noodle could be prepared.

Experiment Example 15: Coloring Example (Sugar-Coated Confectionery Product)

Colored samples of a sugar-coated confectionery product were prepared in accordance with the formulations shown in Table 13.

(Production Method)

(1. Preparation of Sugar-Coating Base)

Granulated sugar (68 parts) and gum arabic (3.4 parts) were mixed together in a powdery form. Ion exchange water (33.6 parts) was weighed in a beaker, then the mixture in a powdery form was added to the ion-exchange water to prepare a solution, and then the solution was heated with an electric heater to adjust the Brix value to 70°. During the heating, the mixture was agitated well while boiling the mixture so as to dissolve the gum arabic therein. The mixture that had been boiled and mixed was placed on a wet towel to distribute air in the mixture evenly, and was then heated again.

(2. Preparation of Colored Sugar-Coating Solution)

The sugar-coating base (Brix: 70°) and a 10% aqueous solution of the emulsion composition of Example 2-1 were mixed together in accordance with the formulations shown in Table 13 to prepare a colored sugar-coating solution.

(3. Preparation of Sugar-Coated Confectionery Product)

Core materials (gum balls) were coated with the colored sugar-coating solution in the conventional manner. A coating pan was set, then the coated core materials were placed in the coating pan, and then the coating pan was rotated. The colored sugar-coating syrup was introduced with a dropper, and then the core materials were rotated. When the surfaces of the sugar-coated core materials were dried, the colored sugar-coating solution was introduced again with the dropper. The rotation and the drying were repeated. The coating with the sugar-coating solution was carried out until the sugar coating ratio reached 4.4%. The sugar coating ratio (%) can be expressed as follows:

sugar coating ratio (%)=(increased mass (g))÷(initial mass (g))×100.

TABLE 13

| FORMULATION (PART(S) BY MASS) | CONCENTRATION OF BETA-CAROTENE | | |
|---|---|---|---|
| | 50 ppm | 250 ppm | 500 ppm |
| 1. SUGAR-COATING SOLUTION | 29.97 | 29.85 | 29.7 |
| 2. 10% AQUEOUS SOLUTION OF EMULSION COMPOSITION OF EXAMPLE 2-1 | 0.03 | 0.15 | 0.3 |
| TOTAL | 30 | 30 | 30 |

Figure 8:
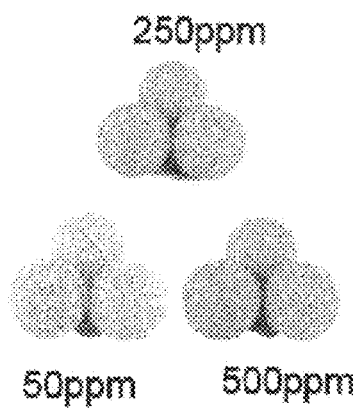
FIG. 8 is a photographic image showing the results of the coloration of a sugar-coated confectionery product with emulsion compositions in Experiment Example 15.

The results are shown in FIG. 8. As shown in FIG. 8, when the emulsion composition of the present invention was used, a uniformly colored sugar-coated confectionery product could be prepared.

Experiment Example 16: Coloring Example (Hard Candy)

Colored samples of a hard candy were prepared in accordance with the formulations shown in Table 14.

(Production Method)

Components 1 to 3 shown in Table 14 were boiled to 190° C. and were then cooled to 120° C. Components 4 to 6 were added to the cooled product, the resultant mixture was mixed uniformly, and was then poured into a mold to shaping the mixture, and then the shaped products were cooled to prepare a hard candy sample.

TABLE 14

| FORMULATION (PART(S) BY MASS) | CONCENTRATION OF BETA-CAROTENE | | |
|---|---|---|---|
| | 50 ppm | 200 ppm | 800 ppm |
| 1. POWDERY REDUCED PALATINOSE (REGISTERED TRADENAME) PNP | 90 | 90 | 90 |
| 2. REDUCED MALTOSE STARCH SYRUP (AMALTY SYRUP) | 16 | 16 | 16 |
| 3. ION-EXCHANGE WATER | 30 | 30 | 30 |
| 4. CITRIC ACID (ANHYDROUS) | 1.3 | 1.3 | 1.3 |
| 5. L-ASCORBIC ACID | 0.02 | 0.02 | 0.02 |
| 6. 10% AQUEOUS SOLUTION OF EMULSION COMPOSITION OF EXAMPLE 2-1 | 0.1 | 0.4 | 1.6 |
| TOTAL | ADJUSTED TO ABOUT 100 BY BOILING | | |

Figure 9:
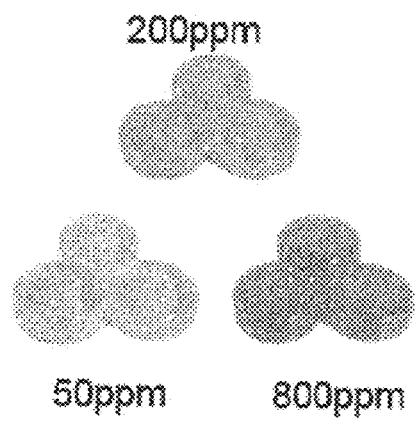
FIG. 9 is a photographic image showing the results of the coloration of hard candy with emulsion compositions in Experiment Example 16.

The results are shown in FIG. 9. As shown in FIG. 9, when the emulsion composition of the present invention was used, a uniformly colored hard candy could be prepared.

Experiment Example 17: Emulsion Compositions

Emulsion compositions were produced in accordance with the formulations shown in Table 15.

Preparatory emulsion compositions, emulsion compositions, and the emulsion compositions after being stored at 60° C. for 7 days were evaluated with respect to the items "D50 (μm)" and "1.3 μm↑". The results are shown in Table 15.

was increased, a phenomenon that the particle diameters in an emulsion composition was reduced was not observed, and a tendency that the emulsion particle diameters in an emulsion composition became large (i.e., a tendency that the emulsion particles were deteriorated) was observed. From these results, it is assumed that it is difficult to reduce the particle diameters of emulsion particles by varying the pressuring conditions to be employed in the homogenization treatment.

Experiment Example 18: Emulsion Compositions

Emulsion compositions were produced in accordance with the formulations shown in Table 16. The emulsion

TABLE 15

| FORMULATION OF EMULSION COMPOSITION (% by mass) | | EXAMPLE | | COMPARATIVE EXAMPLE | | |
|---|---|---|---|---|---|---|
| | | 17-1 | 17-2 | 17-1 | 17-2 | 17-3 |
| OILY PHASE | BETA-CAROTENE | 2.35 | 2.35 | 2.35 | 2.35 | 2.35 |
| | dl-α-TOCOPHEROL | 0.1 | 0.1 | 0.1 | 0.1 | 0.1 |
| | CORN OIL | 5.33 | 5.33 | 5.33 | 5.33 | 5.33 |
| | RICE GERM OIL | 5.72 | 5.72 | 5.72 | 5.72 | 5.72 |
| | TOTAL OF OILY PHASE | 13.5 | 13.5 | 13.5 | 13.5 | 13.5 |
| AQUEOUS PHASE | Gum ghatti | 6 | 6 | 6 | 6 | 6 |
| | Modified starch | 0.75 | 1.5 | — | — | — |
| | GLYCERIN | 38.3 | 38.3 | 38.3 | 38.3 | 38.3 |
| | CITRIC ACID (ANHYDROUS) | 0.2 | 0.2 | 0.2 | 0.2 | 0.2 |
| | L-ASCORBIC ACID | 0.5 | 0.5 | 0.5 | 0.5 | 0.5 |
| | ION-EXCHANGE WATER | 40.75 | 40 | 41.5 | 41.5 | 41.5 |
| | TOTAL OF AQUEOUS PHASE | 86.5 | 86.5 | 86.5 | 86.5 | 86.5 |
| CONTENT OF MODIFIED STARCH RELATIVE TO 100 PARTS BY MASS OF GUM GHATTI (PART(S) BY MASS) | | 12.5 | 25 | 0 | 0 | 0 |
| PREPARATORY EMULSION SOLUTION, D50 (μm) | | 8.99 | 7.05 | 8.99 | 7.82 | 7.82 |
| PREPARATORY EMULSION SOLUTION, 1.3 μm↑ (%) | | 100 | 100 | 100 | 100 | 100 |
| EMULSION COMPOSITION, D50 (μm) | | 0.23 | 0.16 | 0.43 | 0.45 | 0.47 |
| EMULSION COMPOSITION, 1.3 μm↑ (%) | | 0 | 0 | 0 | 0 | 7 |

As shown in Table 15, it was demonstrated that, when gum ghatti and a modified starch were used in combination, an emulsion composition having smaller emulsion particle diameters compared with a case where gum ghatti was used singly could be prepared (Examples 17-1 to 17-2).

Comparative Examples 17-1 to 17-3 were examples in which the pressures to be employed for the homogenization treatment were adjusted to "500 kg/cm², 5 passes", "600 kg/cm², 5 passes" and "700 kg/cm², 5 passes", respectively. Even when the pressure for the homogenization treatment compositions were prepared in the same manner as in the above-mentioned "method for preparing emulsion compositions", except that the formulations of an oily phase and an aqueous phase were altered.

The emulsion compositions immediately after preparation were evaluated with respect to the items "D50 (μm)" and "1.3 μm↑". The results are shown in Table 16.

TABLE 16

| FORMULATION OF EMULSION | | EXAMPLE | |
|---|---|---|---|
| | COMPOSITION (% BY MASS) | 18-1 | 18-2 |
| OILY PHASE | APOCAROTENAL | 3.53 | — |
| | MARIGOLD COLORANT | — | 2.20 |
| | dl-α-TOCOPHEROL | 0.30 | 0.30 |
| | MEDIUM-CHAIN FATTY ACID TRIGLYCERIDE | 18.67 | 20.00 |
| | TOTAL OF OILY PHASE | 22.50 | 22.50 |
| AQUEOUS PHASE | LOW-MOLECULAR-WEIGHT GUM GHATTI | 8.00 | 8.00 |
| | Modified starch | 1.00 | 1.00 |
| | GLYCERIN | 32.00 | 32.00 |
| | LACTIC ACID (50% AQUEOUS SOLUTION) | 0.50 | 0.50 |
| | L-ASCORBIC ACID | 0.50 | 0.50 |
| | ION-EXCHANGE WATER | 35.50 | 32.50 |
| | TOTAL OF AQUEOUS PHASE | 77.50 | 77.50 |
| | CONTENT OF MODIFIED STARCH RELATIVE TO 100 PARTS BY MASS OF LOW-MOLECULAR-WEIGHT GUM GHATTI (PART(S) BY MASS) | 12.5 | 12.5 |
| | EMULSION COMPOSITION, D50 (μm) | 0.19 | 0.39 |
| | EMULSION COMPOSITION, 1.3 μm↑ (%) | 0 | 0 |

From the results shown in Table 16, it was demonstrated that, when low-molecular-weight gum ghatti and a modified starch were used in combination, an emulsion composition having emulsion particle diameters of 1 μm or less could be prepared even when the content of oily components was as high as 22.5% by mass.

Experiment Example 19: Emulsion Compositions

Emulsion compositions were produced in accordance with the formulations shown in Tables 2 and 17.

In the formulations, a plurality of types of low-molecular-weight gum ghatti having different weight average molecular weights were used.

Emulsion compositions were prepared in the same manner as in Example 2-1, except that each of the low-molecular-weight gum ghatti products respectively having the molecular weights shown in Table 17 was used in place of the low-molecular-weight gum ghatti shown in Table 2.

The emulsion compositions were evaluated with respect to the items "D50 (μm)" and "1.3 μm↑" immediately after preparation and after being stored (at 60° C. for 3 days; at 60° C. for 7 days; at 40° C. for 7 days). The results are shown in Table 17.

As apparent from Table 17, when low-molecular-weight gum ghatti having any molecular weight was used, emulsion compositions each having small emulsion particle diameters could be prepared and each of the emulsion compositions retained the emulsion particle diameters at a smaller level even after being stored 60° C. for 7 days.

Experiment Example 20: Emulsion Compositions

Emulsion compositions were produced in accordance with the formulations shown in Table 18. The emulsion compositions were prepared in the same manner as in the above-mentioned "method for preparing emulsion compositions", except that the formulations of an oily phase and an aqueous phase were altered.

The emulsion compositions were evaluated with respect to the items "D50 (μm)" and "1.3 μm↑" immediately after preparation and after being stored at 60° C. for 3 days. The results are shown in Table 18.

TABLE 17

| | | EXAMPLE 19-1 | EXAMPLE 19-2 | EXAMPLE 19-3 | EXAMPLE 19-4 | EXAMPLE 19-5 |
|---|---|---|---|---|---|---|
| MOLECULAR WEIGHT OF GUM GHATTI | | 344,200 | 223,200 | 164,900 | 136,500 | 91,800 |
| IMMEDIATELY AFTER PREPARATION | D50 (μm) | 0.29 | 0.24 | 0.22 | 0.21 | 0.21 |
| 60° C. 3 DAYS | 1.3 μm↑ (%) | 0 | 0 | 0 | 0 | 1 |
| | D50 (μm) | 0.29 | 0.24 | 0.23 | 0.22 | 0.23 |
| 60° C. 7 DAYS | 1.3 μm↑ (%) | 0 | 0 | 0 | 0 | 3 |
| | D50 (μm) | 0.30 | 0.24 | 0.23 | 0.22 | 0.23 |
| | 1.3 μm↑ (%) | 0 | 0 | 0 | 1 | 4 |
| 40° C. 7 DAYS | D50 (μm) | 0.29 | 0.25 | 0.23 | 0.22 | 0.22 |
| | 1.3 μm↑ (%) | 0 | 0 | 0 | 0 | 1 |

TABLE 18

| FORMULATION OF EMULSION | | EXAMPLE | | |
|---|---|---|---|---|
| COMPOSITION (% BY MASS) | | 20-1 | 20-2 | 20-3 |
| OILY PHASE | BETA-CAROTENE | 5.88 | — | — |
| | dl-α-TOCOPHEROL | 0.10 | — | 0.50 |
| | VITAMIN E (TOCOPHEROL ACETATE) | — | 15.00 | — |
| | REDUCED COENZYME Q10 | — | — | 15.00 |
| | MEDIUM-CHAIN FATTY ACID TRIGLYCERIDE | 16.52 | 7.50 | 7.00 |
| | TOTAL OF OILY PHASE | 22.50 | 22.50 | 22.50 |
| AQUEOUS PHASE | LOW-MOLECULAR-WEIGHT GUM GHATTI | 8.00 | 8.00 | 8.00 |
| | Modified starch | 1.00 | 1.00 | 1.00 |
| | GLYCERIN | — | 32.00 | 32.00 |
| | SORBITOL (70% SOLUTION) | 32.00 | — | — |
| | LACTIC ACID (50% AQUEOUS SOLUTION) | 0.50 | 0.50 | 0.50 |
| | L-ASCORBIC ACID | 0.50 | 0.50 | 0.50 |
| | ION-EXCHANGE WATER | 35.50 | 35.50 | 35.50 |
| | TOTAL OF AQUEOUS PHASE | 77.50 | 77.50 | 77.50 |
| | CONTENT OF MODIFIED STARCH RELATIVE TO 100 PARTS BY MASS OF LOW-MOLECULAR-WEIGHT GUM GHATTI (PART(S) BY MASS) | 12.5 | 12.5 | 12.5 |
| | EMULSION COMPOSITION, D50 (μm) | 0.21 | 0.25 | 0.22 |
| | EMULSION COMPOSITION, 1.3 μm↑ (%) | 0 | 0 | 0 |
| | STORED AT 60° C. FOR 3 DAYS, D50 (μm) | 0.22 | 0.26 | 0.22 |
| | STORED AT 60° C. FOR 3 DAYS, 1.3 μm↑ (%) | 2 | 0 | 0 |

From the results shown in Table 18, it was demonstrated that, when low-molecular-weight gum ghatti and a modified starch were used in combination, high stable emulsion compositions each having emulsion particle diameters of 1 μm or less could be prepared even when various formulations were employed.

Emulsion compositions were produced in accordance with the formulations shown in Table 19. The emulsion compositions were prepared in the same manner as in the above-mentioned "method for preparing emulsion compositions", except that the formulations of an oily phase and an aqueous phase were altered.

In the formulations, starches shown in Table 19 were used as the modified starch.

The emulsion compositions were evaluated with respect to the items "D50 (μm)" and "1.3 μm↑" immediately after preparation and after being stored at 60° C. for 3 days. The results are shown in Table 19.

TABLE 19

| FORMULATION OF EMULSION | | EXAMPLE | |
|---|---|---|---|
| COMPOSITION (% BY MASS) | | 21-1 | 21-2 |
| OILY PHASE | BETA-CAROTENE | 5.88 | 5.88 |
| | dl-α-TOCOPHEROL | 0.10 | 0.10 |
| | MEDIUM-CHAIN FATTY ACID TRIGLYCERIDE | 16.52 | 16.52 |
| | TOTAL OF OILY PHASE | 22.50 | 22.50 |
| AQUEOUS PHASE | LOW-MOLECULAR-WEIGHT GUM GHATTI | 8.00 | 8.00 |
| | MODIFIED STARCH (DISTARCH PHOSPHATE) | 1.00 | — |
| | MODIFIED STARCH (HYDROXYPROPYL STARCH) | — | 1.00 |
| | GLYCERIN | 32.00 | 32.00 |
| | LACTIC ACID (50% AQUEOUS SOLUTION) | 0.50 | 0.50 |
| | L-ASCORBIC ACID | 0.50 | 0.50 |
| | ION-EXCHANGE WATER | 35.50 | 35.50 |
| | TOTAL OF AQUEOUS PHASE | 77.50 | 77.50 |
| | CONTENT OF MODIFIED STARCH RELATIVE TO 100 PARTS BY MASS OF LOW-MOLECULAR-WEIGHT GUM GHATTI (PART(S) BY MASS) | 12.5 | 12.5 |
| | EMULSION COMPOSITION, D50 (μm) | 0.39 | 0.41 |
| | EMULSION COMPOSITION, 1.3 μm↑ (%) | 8 | 9 |
| | STORED AT 60° C. FOR 3 DAYS, D50 (μm) | 0.44 | 0.41 |
| | STORED AT 60° C. FOR 3 DAYS, 1.3 μm↑ (%) | 19 | 5 |

As apparent from Table 19, it was demonstrated that, when low-molecular-weight gum ghatti and a modified starch were used in combination, high stable emulsion compositions each having emulsion particle diameters of 1 μm or less, and showing small fluctuations in particle diameters after being stored at 60° C. for 3 days could be prepared regardless of the types of the modified starch.

What is claimed is:

1. A carotenoid emulsion preparation comprising:
water,
an oily component,
low-molecular-weight gum ghatti having a weight average molecular weight of $0.040 \times 10^6$ to $0.60 \times 10^6$, and
a modified starch,
wherein:
- the content of the water is 5 to 60% by mass relative to the whole amount of the composition,
- the content of the oily component is 13% by mass or more relative to the whole amount of the composition,
- the content of the low-molecular-weight gum ghatti is 0.5 to 15% by mass relative to the whole amount of the composition, and
- the content of the modified starch is 100 parts by mass or less relative to 100 parts by mass of the gum ghatti,
- wherein the oily component comprises a carotenoid colorant, and
- wherein the content of the carotenoid colorant is 5% by mass or more relative to the whole amount of the composition.

2. The carotenoid emulsion preparation according to claim 1, wherein the carotenoid colorant is beta-carotene.

* * * * *

UNITED STATES PATENT AND TRADEMARK OFFICE
CERTIFICATE OF CORRECTION

PATENT NO. : 11,523,629 B2
APPLICATION NO. : 17/050344
DATED : December 13, 2022
INVENTOR(S) : Takaaki Ito It is certified that error appears in the above-identified patent and that said Letters Patent is hereby corrected as shown below:

In the Specification

Column 3, Line 45, delete "MODE FOR CARRYING OUT THE INVENTION" and insert -- DETAILED DESCRIPTION --.

Column 25-26, Line 7 (TABLE 5), delete "WELGHT" and insert -- WEIGHT --.

Column 25-26, Line 16 (TABLE 5), delete "WELGHT" and insert -- WEIGHT --.

Column 31-32, Line 7 (TABLE 10-continued), delete "(PUDDLNG" and insert -- (PUDDING --.

Column 39-40, Line 7 (TABLE 19), delete "MOLECUIAR" and insert -- MOLECULAR --.

Signed and Sealed this
Sixth Day of June, 2023

Katherine Kelly Vidal
*Director of the United States Patent and Trademark Office*